(12) United States Patent
Zhuang et al.

(10) Patent No.: US 12,233,209 B2
(45) Date of Patent: Feb. 25, 2025

(54) VENTILATION TREATMENT DEVICE AND VENTILATION-CONTROL METHOD

(71) Applicant: BMC MEDICAL CO., LTD., Beijing (CN)

(72) Inventors: Zhi Zhuang, Beijing (CN); Mingzhao Zhou, Beijing (CN); Erliang Li, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 0 days.

(21) Appl. No.: 18/581,418

(22) Filed: Feb. 20, 2024

(65) Prior Publication Data

US 2024/0207546 A1    Jun. 27, 2024

Related U.S. Application Data

(63) Continuation of application No. 17/789,798, filed as application No. PCT/CN2020/141985 on Dec. 31, 2020, now Pat. No. 11,944,749.

(30) Foreign Application Priority Data

Dec. 31, 2019   (CN) .......................... 201911413191.3

(51) Int. Cl.
*A61M 16/08* (2006.01)
*A61M 16/00* (2006.01)
*A61M 16/20* (2006.01)

(52) U.S. Cl.
CPC ........ *A61M 16/0003* (2014.02); *A61M 16/08* (2013.01); *A61M 16/20* (2013.01)

(58) Field of Classification Search
CPC .......................... A61M 16/0003; A61M 16/08
See application file for complete search history.

(56) References Cited

U.S. PATENT DOCUMENTS

| | | | |
|---|---|---|---|
| 4,506,665 A | 3/1985 | Andrews et al. | |
| 6,343,603 B1 | 2/2002 | Tuck et al. | |
| 8,678,003 B2 | 3/2014 | Darkin et al. | |
| 10,828,454 B2 * | 11/2020 | Harwood | A61M 16/06 |

(Continued)

FOREIGN PATENT DOCUMENTS

| | | |
|---|---|---|
| CN | 103269746 A | 8/2013 |
| CN | 205127060 U | 4/2016 |

(Continued)

*Primary Examiner* — Kevin R Barss
(74) *Attorney, Agent, or Firm* — Bayramoglu Law Offices LLC

(57) ABSTRACT

A tube assembly includes a first tube piece and a second tube piece. The first tube piece includes an inlet end connecting a gas source and an outlet end connecting the second tube piece. The first tube piece includes a discharging hole that is configured so that, in a connecting state, the discharging hole is closed to make the gas to enter the second tube piece, in the separating state, the discharging hole is opened to make the gas to be discharged outside from the discharging hole. The tube assembly includes a valve member that is configured so that, in the connecting state, the valve member opens the outlet end of the first tube piece to make the gas to enter the second tube piece, and in the separating state, the valve member closes the outlet end to make the gas to be discharged outside from the discharging hole.

20 Claims, 14 Drawing Sheets

(56) References Cited

U.S. PATENT DOCUMENTS

| | | | |
|---|---|---|---|
| 2006/0102184 A1 | 5/2006 | Drew et al. | |
| 2006/0249151 A1 | 11/2006 | Gambone | |
| 2010/0229866 A1* | 9/2010 | Sullivan | A61M 16/0875 |
| | | | 128/205.25 |
| 2015/0107585 A1 | 4/2015 | Allum | |
| 2015/0136137 A1 | 5/2015 | Bugamelli et al. | |
| 2016/0310690 A1 | 10/2016 | Summers et al. | |
| 2018/0250487 A1 | 9/2018 | Hodges et al. | |
| 2023/0044299 A1* | 2/2023 | Zhuang | A61M 16/0816 |
| 2024/0131297 A1* | 4/2024 | Kleinstern | A61M 16/0875 |

FOREIGN PATENT DOCUMENTS

| | | |
|---|---|---|
| CN | 106029146 A | 10/2016 |
| CN | 107405509 A | 11/2017 |
| CN | 208610414 U | 3/2019 |
| CN | 209252279 U | 8/2019 |
| CN | 209734715 U | 12/2019 |
| EP | 1674123 A1 | 6/2006 |
| JP | 2012011243 A | 1/2012 |
| JP | 2014519927 A | 8/2014 |
| JP | 2017508494 A | 3/2017 |
| WO | 2008104004 A1 | 8/2008 |
| WO | 2012174602 A1 | 12/2012 |
| WO | 2015125080 A1 | 8/2015 |
| WO | 2017044392 A1 | 3/2017 |
| WO | 2017049357 A1 | 3/2017 |

* cited by examiner

VENTILATION TREATMENT DEVICE AND VENTILATION-CONTROL METHOD

CROSS REFERENCE TO RELEVANT APPLICATIONS

This application is a continuation of application Ser. No. 17/789,798, filed on Jun. 29, 2022, which is a national stage entry of International Application No. PCT/CN2020/141985, filed on Dec. 31, 2020, which is based upon and claims priority to Chinese Patent Application No. 201911413191.3, filed on Dec. 31, 2019, the entire contents of which are incorporated herein by reference.

TECHNICAL FIELD

The present disclosure relates to the technical field of ventilation treatment, and more particularly, to a ventilation-treatment apparatus and a ventilation-treatment method.

BACKGROUND

The existing ventilation-treatment apparatus generally includes a mainframe for generating treatment gas, a patient-interface device, and a ventilation pipeline connecting a mainframe and the patient-interface device. The patient-interface device generally includes a breathing mask such as a nasal mask, an oral-nasal mask, a nasal pillow mask and a full-surface mask. A typical structure of the breathing mask includes a frame, a pad, a bent pipe and a head band. The pad is fixed to the frame and forms the respiratory cavity with the frame. One end of the bent pipe is connected to the ventilation pipeline, and the other end is connected to the frame to deliver the treatment gas from the mainframe into the respiratory cavity. The head band is connected to the head of the patient to fix the breathing mask to the head of the patient. In usage, the pad contacts the face of the patient and implements the sealing with the surface, and the mouth and/or the nose of the patient is put inside the respiratory cavity.

However, the above-described ventilation-treatment apparatus has the following problems. In nighttime treatment, some unconscious actions can (such as turning over or rotating head) affect the reliability of the ventilation treatment when the patient is in sleep. In addition, when the patient requires to pause the treatment, he is required to shut down the mainframe, and take down the breathing mask or separate the ventilation pipeline and the mainframe, otherwise, the device will have a very large gas-leakage noise, which affects the rest of the company. When the patient requires to restart the treatment, he is required to wear the breathing mask or connect the ventilation pipeline to the mainframe and start up the mainframe, therefore, the overall comfort of the patient during treatment can be seriously affected due to such tedious operations in the process.

SUMMARY

An object of the present disclosure is to provide a ventilation-treatment apparatus and a ventilation-treatment method, to solve the above problems.

In order to achieve the above object, an aspect of the present disclosure provides a ventilation-treatment apparatus, wherein the ventilation-treatment apparatus includes:

a headrest, wherein the headrest includes a first chamber, and a gas inlet and a first gas hole that communicate with the first chamber, the gas inlet is for a gas from a gas source to enter the first chamber, and a first valve assembly for opening and closing the first gas hole is disposed at the first gas hole; and a patient-interface device, wherein the patient-interface device includes a main body having a respiratory cavity, and a head band connected to the main body, the head band includes a second chamber, a gas outlet and a second gas hole that communicates with the second chamber, the gas outlet communicates with the second chamber and the respiratory cavity, and a second valve assembly for opening and closing the second gas hole (222) is disposed at the second gas hole (222); and the ventilation-treatment apparatus is configured for, when the first valve assembly and the second valve assembly contact, opening the first gas hole and the second gas hole, to make the first chamber and the second chamber to be communicated, and when the first valve assembly and the second valve assembly are separated, closing the first gas hole and the second gas hole.

Optionally, the first valve assembly includes a first valve body, and the first valve body penetrates the first gas hole and is capable of moving reciprocatingly relative to the first gas hole and in an axial direction of the first gas hole, to move between a first opening position of opening the first gas hole and a first closing position of closing the first gas hole;

the second valve assembly includes a second valve body, and the second valve body penetrates the second gas hole and is capable of moving reciprocatingly relative to the second gas hole and in an axial direction of the second gas hole, to move between a second opening position of opening the second gas hole and a second closing position of closing the second gas hole;

when the first valve body and the second valve body contact, the first valve body moves to the first opening position, and the second valve body moves to the second opening position; and when the first valve body and the second valve body are separated, the first valve body moves to the first closing position, and the second valve body moves to the second closing position.

Optionally, the first valve assembly includes a first electrical driving member, and the first electrical driving member is configured to be capable of, when the first valve body and the second valve body contact, controlling the first valve body to move to the first opening position, and, when the first valve body and the second valve body are separated, controlling the first valve body to move to the first closing position; and the second valve assembly includes a second electrical driving member, and the second electrical driving member is configured to be capable of, when the second valve body and the first valve body contact, controlling the second valve body to move to the second opening position, and, when the second valve body and the first valve body are separated, controlling the second valve body to move to the second closing position.

Optionally, the first valve assembly includes a first elastic member, and the first elastic member is configured to be capable of, being compressed to allow the first valve body to move to the first opening position when the first valve body is under a pressure, and, being restored to drive the first valve body to move to the first closing position when the first valve body is released from the pressure; and the second valve assembly comprises a second elastic member, and the second elastic member is configured to be capable of being compressed to allow the second valve body to move to the second opening position when the second valve body is under a pressure, and, being restored to drive the second valve body to move to the second closing position when the second valve is released from the pressure.

Optionally, the first valve body includes a first penetrating part, and a first covering part and a first stopping part that are connected to two ends of the first penetrating part, respectively, the first penetrating part penetrates the first gas hole and forms a radial gap with the first gas hole, the first covering part and the first stopping part are located at an inner side and an outer side of the first gas hole, respectively, the first covering part is configured for covering and opening the radial gap, the first elastic member is a compression spring nested to the first penetrating part, and the first elastic member is connected between the first stopping part and a periphery of the first gas hole; and the second valve body includes a second penetrating part, and a second covering part and a second stopping part that are connected to two ends of the second penetrating part, the second penetrating part penetrates the second gas hole and forms a radial gap with the second gas hole, the second covering part and the second stopping part are located at an inner side and an outer side of the second gas hole respectively, the second covering part is configured for covering and opening the radial gap, the second elastic member is a compression spring nested to the second penetrating part, and the second elastic member is connected between the second stopping part and a periphery of the second gas hole.

Optionally, the ventilation-treatment apparatus includes a guiding member configured for guiding the contacting between the first valve assembly and the second valve assembly; and/or the ventilation-treatment apparatus includes a sealing member, and the scaling member is for, when the first valve assembly and the second valve assembly contact, scaling the communication between the first gas hole and the second gas hole.

Optionally, the guiding member includes a first magnet disposed at a periphery of the first gas hole and a second magnet disposed at a periphery of the second gas hole, and magnetic poles of the first magnet and magnetic poles of the second magnet are set oppositely and correspondingly.

Optionally, the headrest is disposed with a protrusion, a slot is disposed at a top of the protrusion, the first gas hole is disposed in the slot, the first magnet extends in a circumferential direction of a slot opening of the slot, the second magnet extends in the periphery of the second gas hole, and the slot opening of the slot is scalable with the head band by attraction between the first magnet and the second magnet; or the head band is disposed with a protrusion, a slot is disposed at a top of the protrusion, the second gas hole is disposed in the slot, the second magnet extends in a circumferential direction of a slot opening of the slot, the first magnet extends in the periphery of the first gas hole, and the slot opening of the slot is scalable with the headrest by attraction between the first magnet and the second magnet.

Optionally, the guiding member includes a protrusion and a depression that match, the protrusion is disposed at one of the headrest and the head band, the depression is disposed at the other of the headrest and the head band, the first gas hole is disposed at one of the protrusion and the depression, and the second gas hole is disposed at the other of the protrusion and the depression.

Optionally, the sealing member is a sealing ring, and the sealing ring is nested outside the protrusion or inside the depression, to seal the radial gap between the protrusion and the depression when the protrusion is embedded inside the depression.

Optionally, the headrest is disposed with the plurality of first gas holes, the head band is disposed with the plurality of second gas holes, and when the head band and the headrest contact, and a part of the second gas holes are capable of being selectively in communication with a part of the first gas holes one to one correspondingly; and/or the ventilation-treatment apparatus includes a tube assembly, and the tube assembly is connected to the main body to communicate the respiratory cavity with the gas source.

Optionally, the tube assembly includes a first tube piece and a second tube piece, the tube assembly is provided with a connecting state in which the first tube piece and the second tube piece are coaxially plug-connected and a separating state in which the first tube piece and the second tube piece are separate from each other, and the first tube piece has an inlet end for connecting the gas source and an outlet end for connecting the second tube piece;

the first tube piece has a discharging hole, and the discharging hole is configured so that, in the connecting state, the discharging hole is closed to make the gas from the gas source to enter the second tube piece, and in the separating state, the discharging hole is opened to make the gas from the gas source to be discharged from the discharging hole to the external; and the tube assembly includes a valve member, and the valve member is configured so that, in the connecting state, the valve member opens the outlet end of the first tube piece to make the gas from the gas source to enter the second tube piece, and in the separating state, the valve member closes the outlet end to make the gas from the gas source to be discharged from the discharging hole to the external.

Another aspect of the present disclosure provides a ventilation-treatment method, wherein the method is performed by using the ventilation-treatment apparatus stated above, the ventilation-treatment apparatus further includes a mainframe serving as the gas source, and the method includes the following steps:

generating a first signal when the first valve assembly and the second valve assembly contact, and according to the first signal, controlling the mainframe to start up or increase a ventilation capacity; and/or generating a second signal when the first valve assembly and the second valve assembly are separated, and according to the second signal, controlling the mainframe to shut down or reduce a ventilation capacity.

By using the above technical solutions, when the ventilation-treatment apparatus according to the present disclosure is being used, when the head band and the headrest contact, the first valve assembly and the second valve assembly contact to open the first gas hole and the second gas hole, thereby the first chamber communicates with the second chamber, whereby the gas entering the first chamber from the gas source may enter the second chamber and further enter the respiratory cavity of the patient-interface device for the patient to inhale. When the head band and the headrest are separated, the first valve assembly and the second valve assembly are separated to close the first gas hole and the second gas hole, thereby preventing the gas inside the first chamber and the second chamber from flowing out via the first gas hole and the second gas hole, respectively. Therefore, the operations on the mainframe, the patient-interface device and the ventilation pipeline when the treatment is paused can be omitted, to implement simple operation and anytime usage which can improve the reliability of the ventilation treatment and the comfort of the patient in the treatment process.

The other characteristics and advantages of the present disclosure will be described in detail in the subsequent section of DETAILED DESCRIPTION OF THE EMBODIMENTS.

The above description is merely a summary of the technical solutions of the present disclosure. In order to more clearly know the elements of the present disclosure to enable the implementation according to the contents of the description, and in order to make the above and other purposes, features and advantages of the present disclosure more apparent and understandable, the particular embodiments of the present disclosure are disposed below.

BRIEF DESCRIPTION OF THE DRAWINGS

In order to more clearly illustrate the technical solutions of the embodiments of the present disclosure or the prior art, the figures that are required to describe the embodiments or the prior art will be briefly introduced below. Apparently, the figures that are described below are embodiments of the present disclosure, and a person skilled in the art can obtain other figures according to these figures without paying creative work.

The drawings are intended to provide a further understanding of the present disclosure, and constitute part of the description. The drawings are intended to interpret the present disclosure together with the following particular embodiments, and do not function to limit the present disclosure. In the drawings.

DETAILED DESCRIPTION OF THE EMBODIMENTS

The particular embodiments of the present disclosure will be described in detail below with reference to the drawings. It should be understood that the particular embodiments described herein are merely intended to describe and interpret the present disclosure, and are not intended to limit the present disclosure.

Figure 2:
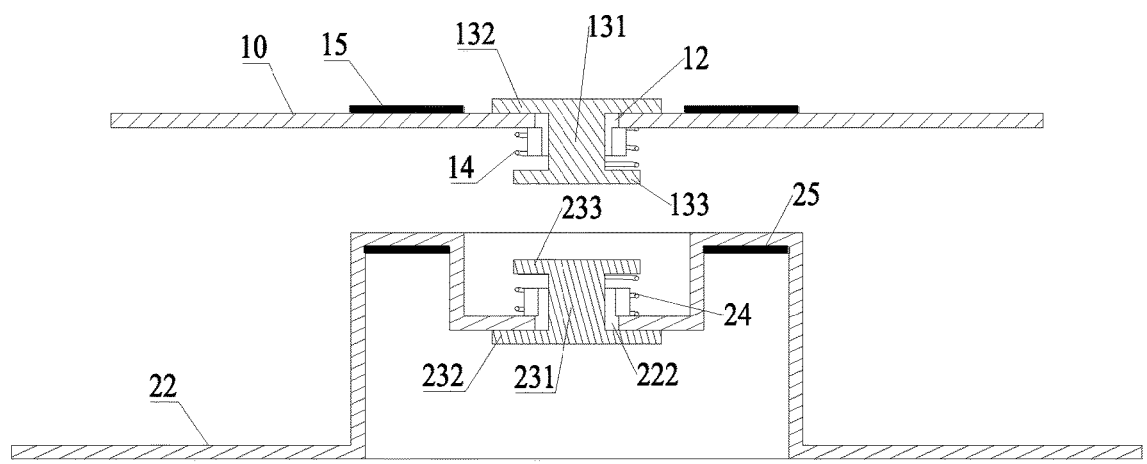
FIG. 2 is a schematic diagram of an embodiment of, when the first valve assembly and the second valve assembly are separated, closing the first gas hole and the second gas hole according to the present disclosure.

In the present disclosure, unless stated otherwise, the used words of orientation, such as "upper", "lower", "top" and "bottom", generally refer to the orientations shown in FIG. 2, and "inner" and "outer" refer to the interior and the exterior with respect to the contours of the components themselves.

An aspect of the present disclosure provides a ventilation-treatment apparatus, wherein the ventilation-treatment apparatus includes:

a headrest 10, wherein the headrest 10 includes a first chamber 11, and a gas inlet and a first gas hole 12 that communicate with the first chamber 11, the gas inlet is for a gas from a gas source to enter the first chamber 11, and the first gas hole 12 is disposed with a first valve assembly for opening and closing the first gas hole 12; and a patient-interface device 20, wherein the patient-interface device 20 includes a main body 21 having a respiratory cavity, and a head band 22 connected to the main body 21, the head band 22 includes a second chamber 221, and a gas outlet and a second gas hole 222 that communicate with the second chamber 221, the gas outlet communicates with the second chamber 221 and the respiratory cavity, and the second gas hole 222 is disposed with a second valve assembly for opening and closing the second gas hole 222; and the ventilation-treatment apparatus is configured for, when the first valve assembly and the second valve assembly contact, opening the first gas hole 12 and the second gas hole 222, to make the first chamber 11 communicate with the second chamber 221, and when the first valve assembly and the second valve assembly are separated, closing the first gas hole 12 and the second gas hole 222.

By using the above technical solution, when the ventilation-treatment apparatus according to the present disclosure is being used, when the head band 22 and the headrest 10 contact, the first valve assembly and the second valve assembly contact to open the first gas hole 12 and the second gas hole 222, thereby communicating the first chamber 11 with the second chamber 221, whereby the gas entering the first chamber 11 from the gas source may enter the second chamber 221 and further enter the respiratory cavity of the patient-interface device 20 for the patient to inhale. When the head band 22 and the headrest 10 are separated, the first valve assembly and the second valve assembly are separated to close the first gas hole 12 and the second gas hole 222, thereby preventing the gas inside the first chamber 11 and the second chamber 221 from flowing out via the first gas hole 12 and the second gas hole 222, respectively. Therefore, the operations on the mainframe, the patient-interface device and the ventilation pipeline when the treatment is paused may be omitted, to implement simple operation and anytime usage which can improve the reliability of the ventilation treatment and the comfort of the patient in the treatment process.

In the above description, the first valve assembly and the second valve assembly may be any structure that may implement the function of opening and closing the gas holes.

According to an embodiment of the present disclosure, the first valve assembly may include a first valve body 13, and the first valve body 13 penetrates the first gas hole 12 and is capable of moving reciprocatingly relative to the first gas hole (12) and in an axial direction of the first gas hole (12), to move between a first opening position of opening the first gas hole (12) and a first closing position of closing the first gas hole (12); and the second valve assembly may include a second valve body 23, and the second valve body 23 penetrates the second gas hole 222 and is capable of moving reciprocatingly relative to the second gas hole (222) and in an axial direction of the second gas hole (222), to move between a second opening position of opening the second gas hole (222) and a second closing position of closing the second gas hole (222). When the first valve body 13 and the second valve body 23 contact, the first valve body 13 and the second valve body 23 move to the first opening position and the second opening position, respectively; and when the first valve body 13 and the second valve body 23 are separated, the first valve body 13 and the second valve body 23 move to the first closing position and the second closing position, respectively.

In the above description, the movement of the first valve body 13 and the second valve body 23 may adopt pressure driving, electric driving or any other suitable manner.

Particularly, according to an embodiment of the present disclosure, the first valve assembly may include a first electrical driving member, and the first electrical driving member is configured to be capable of, when the first valve body 13 and the second valve body 23 contact, controlling the first valve body 13 to move to the first opening position, and, when the first valve body 13 and the second valve body 23 are separated, controlling the first valve body 13 to move to the first closing position; and the second valve assembly may include a second electrical driving member, and the second electrical driving member is configured to be capable of, when the second valve body 23 and the first valve body 13 contact, controlling the second valve body 23 to move to the second opening position, and, when the second valve body 23 and the first valve body 13 are separated, controlling the second valve body 23 to move to the second closing position. In other words, in the present embodiment, the movement of the first valve body 13 and the second valve body 23 is electrically driven, and the first valve body 13 and the second valve body 23 may be electrically operated valves.

According to another embodiment of the present disclosure, the headrest 10 and the head band 22 may be made to squeeze when contacting each other (for example, by the effect of the weight of the head of the patient), whereby the movement of the first valve body 13 and the second valve body 23 is implemented by the effect of the mutual squeezing. In other words, in the present embodiment, the movement of the first valve body 13 and the second valve body 23 is pressure-driven. The first valve assembly may include a first elastic member 14, and the first valve assembly comprises a first elastic member (14), and the first elastic member (14) is configured to be capable of, being compressed to allow the first valve body (13) to move to the first opening position when the first valve body is under a pressure, and, being restored to drive the first valve body (13) to move to the first closing position when the first valve body (13) is released from the pressure; and the second valve assembly comprises a second elastic member (24), and the second elastic member (24) is configured to be capable of being compressed to allow the second valve body (23) to move to the second opening position when the second valve body (23) is under a pressure, and, being restored to drive the second valve body (23) to move to the second closing position when the second valve is released from the pressure.

In the present disclosure, the first valve body 13 and the second valve body 23 may have any suitable structures. According to an embodiment of the present disclosure, as shown in FIGS. 2 to 5, the first valve body 13 includes a first penetrating part 131, and a first covering part 132 and a first stopping part 133 that are connected to the two ends of the first penetrating part 131, the first penetrating part 131 penetrates the first gas hole 12 and forms a radial gap with the first gas hole 12, the first covering part 132 and the first stopping part 133 are located at the inner side and the outer side of the first gas hole 12, respectively, the first covering part 132 is for covering and opening the radial gap, the first stopping part 133 is for preventing the first valve body 13 from disengaging the first gas hole 12, the second valve body 23 includes a second penetrating part 231, and a second covering part 232 and a second stopping part 233 that are connected to the two ends of the second penetrating part 231, the second penetrating part 231 penetrates the second gas hole 222 and forms a radial gap with the second gas hole 222, the second covering part 232 and the second stopping part 233 are located at the inner side and the outer side of the second gas hole 222, respectively, the second covering part 232 is for covering and opening the radial gap, and the second stopping part 233 is for preventing the second valve body 23 from disengaging the second gas hole 222.

Figure 6:
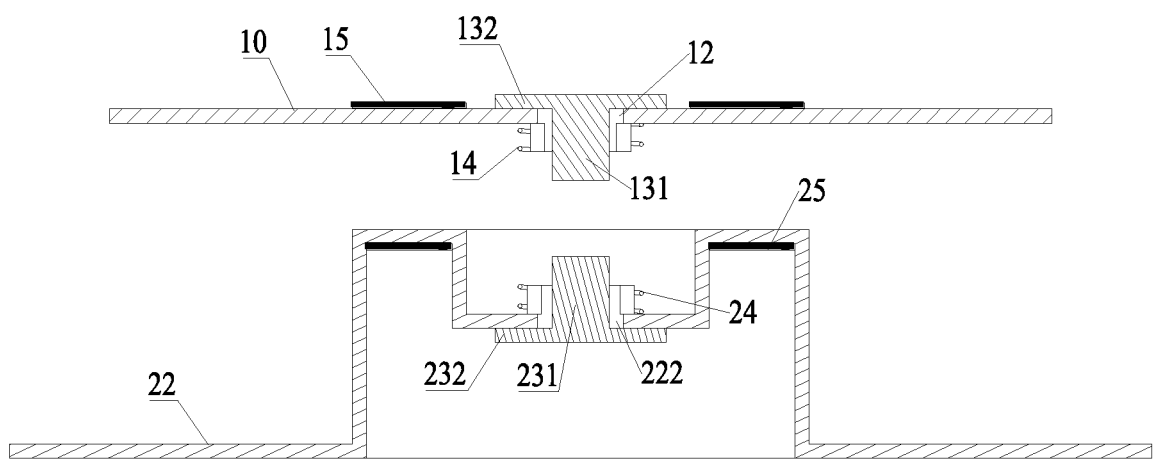
FIG. 6 is a schematic diagram of yet another embodiment of, when the first valve assembly and the second valve assembly are separated, closing the first gas hole and the second gas hole according to the present disclosure.

In the above embodiment, the first elastic member 14 may be a compression spring nested to the first penetrating part 131, and the first elastic member 14 may be connected between the first stopping part 133 and the periphery of the first gas hole 12. The first elastic member 14 may also be configured that one end is connected to the first penetrating part 131, and the other end is connected to the periphery of the first gas hole 12 (as shown in FIG. 2), in which case the first valve body 13 may include merely the first penetrating part 131 and the first covering part 132 (as shown in FIG. 6). The second elastic member 24 may be a compression spring nested to the second penetrating part 231, and the second elastic member 24 may be connected between the second stopping part 233 and the periphery of the second gas hole 222. The second elastic member 24 may also be configured that one end is connected to the second penetrating part 231, and the other end is connected to the periphery of the second gas hole 222 (as shown in FIG. 2), in which case the second valve body 23 may include merely the second penetrating part 231 and the second covering part 232 (as shown in FIG. 6).

Figure 3:
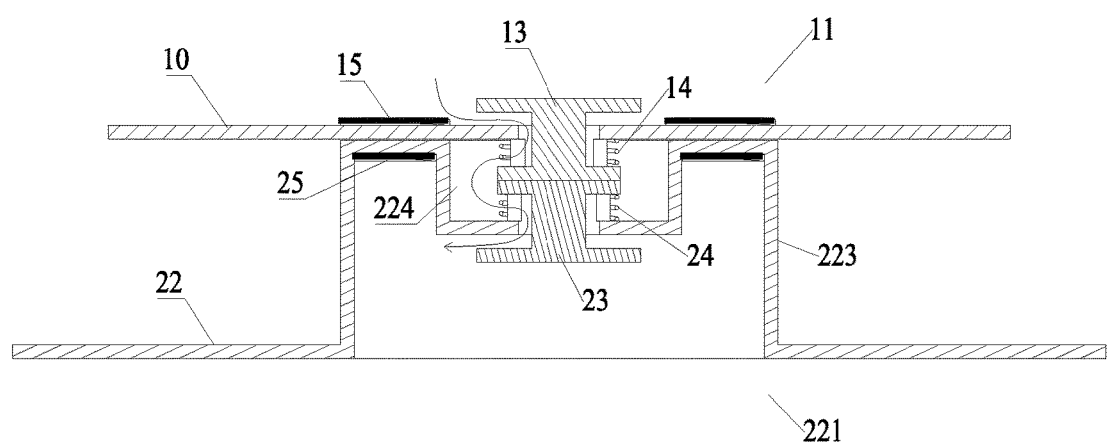
FIG. 3 is a schematic diagram of, when the first valve assembly and the second valve assembly contact, opening the first gas hole and the second gas hole in FIG. 2.

In usage, when the first valve body 13 and the second valve body 23 are contacting and squeezing each other, as shown in FIG. 3, the first valve body 13 is applied an upward force and thus moves upwardly relatively to the first gas hole 12, whereby the first covering part 132 gets further away from the first gas hole 12 and thus opens the radial gap between the first penetrating part 131 and the first gas hole 12, and the first elastic member 14 is further compressed; and the second valve body 23 is applied a downward force and thus moves downwardly relatively to the second gas hole 222, whereby the second covering part 232 gets further away from the second gas hole 222 and thus opens the radial gap between the second penetrating part 231 and the second gas hole 222, and the second elastic member 24 is further compressed. In this case, as shown by the arrow in FIG. 3, the gas inside the first chamber 11 may enter the second chamber 221 via the two radial gaps. Certainly, the gas inside the second chamber 221 may enter the first chamber 11 via the two radial gaps. When the first valve body 13 and the second valve body 23 are separated from each other, as shown in FIG. 2, the first valve body 13 moves downwardly relatively to the first gas hole 12 by the effect of the restoration of the first elastic member 14, whereby the first covering part 132 gets closer to the first gas hole 12 and thus covers the radial gap between the first penetrating part 131 and the first gas hole 12; and the second valve body 23 moves upwardly relatively to the second gas hole 222 by the effect of the restoration of the second elastic member 24, whereby the second covering part 232 gets closer to the second gas hole 222 and thus covers the radial gap between the second penetrating part 231 and the second gas hole 222.

In the present disclosure, the ventilation-treatment apparatus may further include a guiding member for guiding the contacting between the first valve assembly and the second valve assembly.

According to an embodiment of the guiding member according to the present disclosure, the guiding member may include a first magnet 15 disposed at the periphery of the first gas hole 12 and a second magnet 25 disposed at the periphery of the second gas hole 222, and the magnetic poles of the first magnet 15 and the magnetic poles of the second magnet 25 are set oppositely and correspondingly. When the headrest 10 and the head band 22 contact, the first magnet 15 may attract the second magnet 25, whereby the first valve assembly and the second valve assembly are aligned and contacted. In addition, the first magnet 15 and the second magnet 25 that are attracted together may seal the communication between the first gas hole 12 and the second gas hole 222. It should be noted that the first magnet 15 may be disposed at the inner side or the outer side of the periphery of the first gas hole 12, and the second magnet 25 may be disposed at the inner side or the outer side of the periphery of the second gas hole 222. Preferably, as shown in FIG. 2, the first magnet 15 is disposed on the inner side of the periphery of the first gas hole 12, and the second magnet 25 is disposed on the inner side of the periphery of the second gas hole 222, which may prevent damaging or falling of the first magnet 15 and the second magnet 25 after long-term usage of and friction between the headrest 10 and the head band 22.

Optionally, as shown in FIGS. 2 and 3, the head band 22 may be disposed with a protrusion 223, a slot 224 is disposed at the top of the protrusion 223, the second gas hole 222 is disposed in the slot 224, the second magnet 25 extends in the circumferential direction of the slot opening of the slot 224, the first magnet 15 extends in the periphery of the first gas hole 12, and the slot opening of the slot 224 is scalable with the headrest 10 by the attraction between the first magnet 15 and the second magnet 25. Such a configuration may further improve the leak proofness of the communication between the first gas hole 12 and the second gas hole 222. In addition, it may be understood that, in another embodiment, the protrusion 223 may also be disposed at the headrest 10. In this case, the first magnet 15 extends in the circumferential direction of the slot opening of the slot 224, the second magnet 25 extends in the periphery of the second gas hole 222, and the slot opening of the slot 224 is scalable with the head band 22 by the attraction between the first magnet 15 and the second magnet 25.

In the above embodiment, the first electrical driving member and the second electrical driving member may be configured for, when the first magnet 15 and the second magnet 25 are attracting, controlling the first valve body 13 and the second valve body 23 to move to the opening position, and, when the first magnet 15 and the second magnet 25 are separated, controlling the first valve body 13 and the second valve body 23 to move to the closing position.

Figure 4:
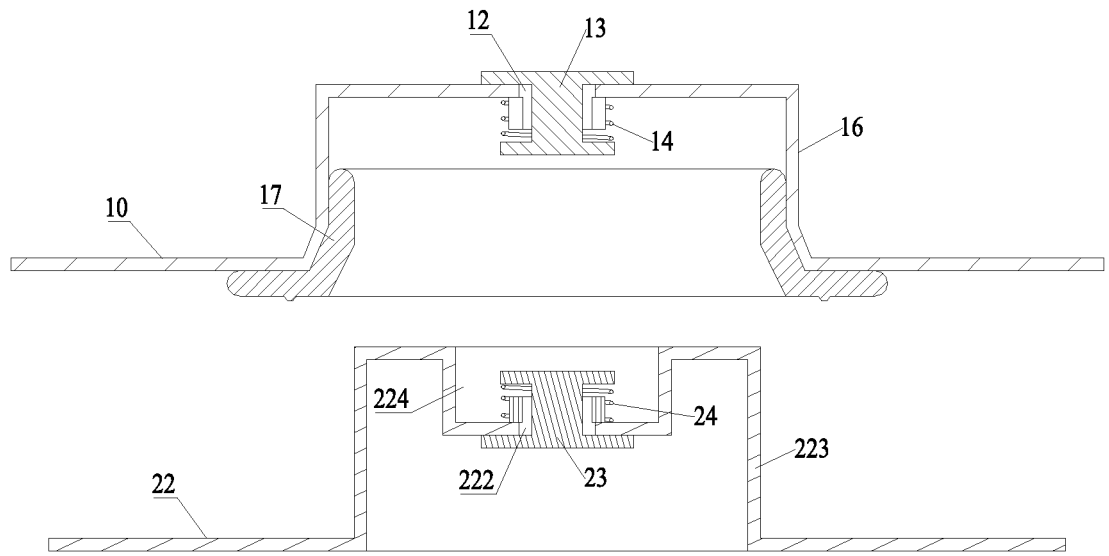
FIG. 4 is a schematic diagram of another embodiment of, when the first valve assembly and the second valve assembly are separated, closing the first gas hole and the second gas hole according to the present disclosure.
Figure 5:
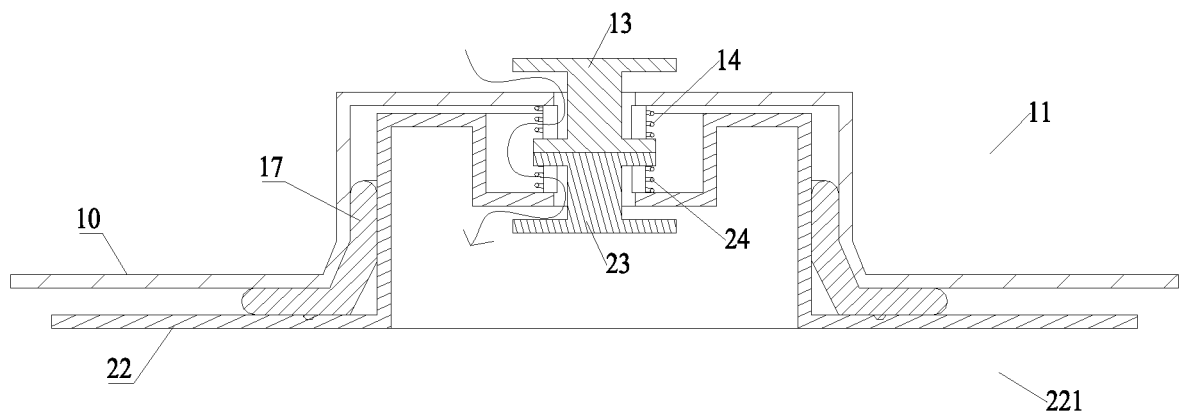
FIG. 5 is a schematic diagram of, when the first valve assembly and the second valve assembly contact, opening the first gas hole and the second gas hole in FIG. 4.

According to another embodiment of the guiding member according to the present disclosure, as shown in FIGS. 4 and 5, the guiding member may include a protrusion 223 and a depression 16 that match, the protrusion 223 is disposed at one of the headrest 10 and the head band 22, the depression 16 is disposed at the other of the headrest 10 and the head band 22, the first gas hole 12 is disposed at one of the protrusion 223 and the depression 16, and the second gas hole 222 is disposed at the other of the protrusion 223 and the depression 16. It should be noted that a slot 224 may be disposed at the top of the protrusion 223, and the first gas hole 12 or the second gas hole 222 is disposed in the slot 224. When the headrest 10 and the head band 22 contact, the protrusion 223 may be embedded into the depression 16, whereby the first valve assembly and the second valve assembly are aligned and contacted. In addition, the protrusion 223 and the depression 16 that are embedded into each other may further improve the leak proofness of the communication between the first gas hole 12 and the second gas hole 222. Certainly, the first magnet 15 and the second magnet 25 may also be further disposed at the protrusion 223 and the depression 16, respectively.

In the present disclosure, in order to ensure the leak proofness of the communication between the first gas hole 12 and the second gas hole 222, the ventilation-treatment apparatus may include a sealing member, and the scaling member is for, when the first valve assembly and the second valve assembly contact, sealing the communication between the first gas hole 12 and the second gas hole 222. Particularly, in the embodiment shown in FIGS. 1 and 2, the scaling member may be formed by the first magnet 15 and the second magnet 25, the scaling member may also be formed by a sealing ring that is nested outside the protrusion 223 and extends beyond the upper end surface of the protrusion 223, and when the first valve assembly and the second valve assembly contact, the sealing ring may contact and squeeze the periphery of the first gas hole 12 to implement the sealing. In the embodiment shown in FIGS. 3 and 4, the scaling member may be a scaling ring 17, and the sealing ring 17 is nested outside the protrusion 223 or inside the depression 16, to, when the protrusion 223 is embedded inside the depression 16, seal the radial gap between the protrusion 223 and the depression 16. The scaling ring 17 may be a silica-gel piece, and when the protrusion 223 is embedded inside the depression 16, the sealing ring 17 is properly squeezed to implement the scaling. In addition, in the structure of the sealing ring shown in FIGS. 4 and 5, the sealing ring 17 may serve to guide the protrusion 223 to be embedded into the depression 16.

In the above embodiment, the mode of the electric driving of the movement of the first valve body 13 and the second valve body 23 may include: when the protrusion 223 is embedded inside the depression 16, forming an electrifying loop or triggering a contact switch, and in turn controlling the first valve body 13 and the second valve body 23 to move to the opening position; and when the protrusion 223 is separated from the depression 16, disconnecting the electrifying loop or triggering a contact switch, and in turn controlling the first valve body 13 and the second valve body 23 to move to the closing position.

In the present disclosure, the headrest 10 may be disposed with a plurality of first gas holes 12, the head band 22 may be disposed with a plurality of second gas holes 222, and when the head band 22 and the headrest 10 contact, and a part of the second gas holes 222 are capable of being selectively in communication with a part of the first gas holes 12 one to one correspondingly. In other words, no matter whether the headrest 10 and the head band 22 locally contact or totally contact, as long as they contact, the first gas hole 12 and the second gas hole 222 at the correspondingly contacting parts may be in communication with each other to make the gas inside the headrest 10 to enter the head band 22, while the first gas hole 12 and the second gas hole 222 at the no-contacting area are closed, whereby no gas leakage happens. Accordingly, the ventilation-treatment apparatus according to the present disclosure, in the process of nighttime treatment, no matter whether the patient turns the body, turns the head or performs another action, may perform the ventilation treatment as long as the head band 22 contacts the headrest 10, which may effectively ensure the reliability of the ventilation treatment, and improve the flexibility of the usage of the ventilation-treatment apparatus.

Figure 1:
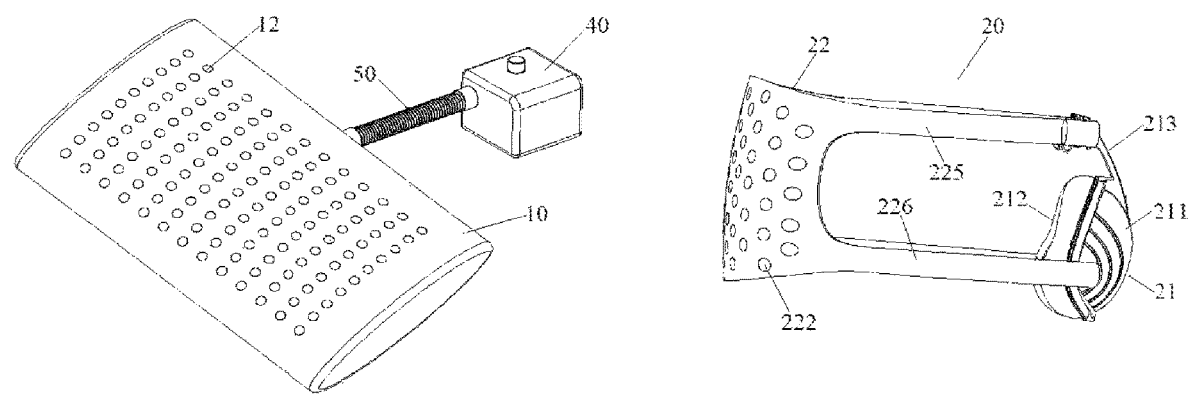
FIG. 1 is a schematic diagram of an embodiment of the ventilation-treatment apparatus according to the present disclosure, wherein the head band and the headrest are in the separating state.
Figure 8:
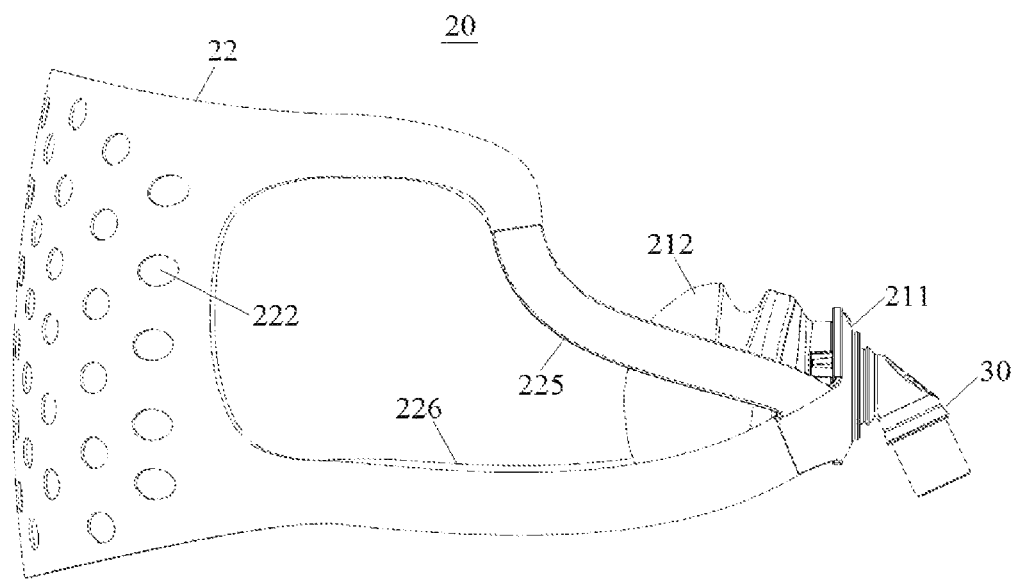
FIG. 8 is a schematic diagram of another embodiment of the patient-interface device according to the present disclosure.
Figure 9:
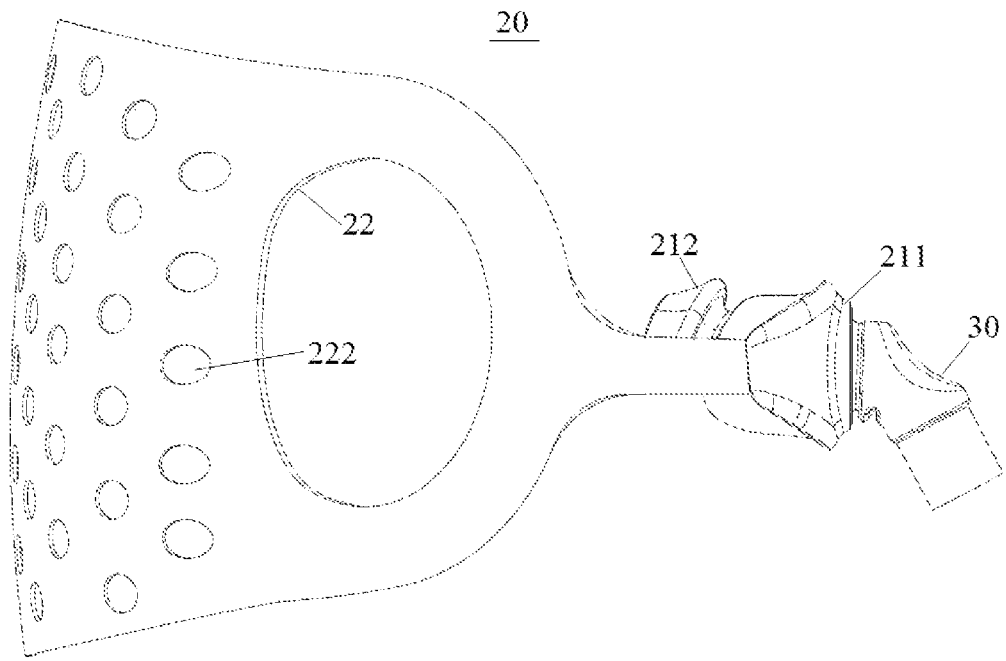
FIG. 9 is a schematic diagram of yet another embodiment of the patient-interface device according to the present disclosure.

In the present disclosure, the patient-interface device 20 may be a breathing mask such as a nasal mask, an oral-nasal mask, a nasal pillow mask and a full-surface mask. For example, as shown in FIGS. 1 and 8-9, the main body 21 of the patient-interface device 20 may include a frame 211 and a pad 212, the pad 212 is mounted to the frame 211 and defines the respiratory cavity with the frame 211, and the head band 22 is connected to the frame 211. The head band 22 may include a main head-band body and a connecting band for connecting the main head-band body to the frame 211, the main head-band body may cover the afterbrain and the two lateral sides of the head of the patient, the second chamber 221 is defined by the main head-band body, and the connecting band defines a communicating cavity for communicating the second chamber 221 and the respiratory cavity. As shown in FIG. 6, the frame 211 may be disposed with a connecting opening 214 for the connecting band to connect and communicate the respiratory cavity and the communicating cavity.

Optionally, the connecting band may include an upper side band 225 and a lower side band 226, both of the upper side band 225 and the lower side band 226 may be connected to the frame 211 (as shown in FIG. 8), and at least one of the upper side band 225 and the lower side band 226 has the communicating cavity.

In addition, in the embodiment shown in FIG. 1, the main body 21 may also include a forehead support 213 connected to the frame 211, the upper side band 225 is connected to the forehead support 213, and the lower side band 226 is connected to the frame 211. In this case, if the communicating cavity is to be disposed at the upper side band 225, the forehead support 213 may be disposed with a hollow structure that communicates the communicating cavity with the respiratory cavity.

In the present disclosure, in order to prevent the headrest 10 and the head band 22 from being crushed to block the gas flowing, a honeycomb component or another supporting component may be disposed inside the headrest 10 and the head band 22. That also facilitates improving the comfort of the head.

In the present disclosure, as shown in FIG. 1, the ventilation-treatment apparatus may further include a mainframe 40 serving as the gas source and a ventilation pipeline 50 for communicating the mainframe 40 with the headrest 10.

Figure 7:
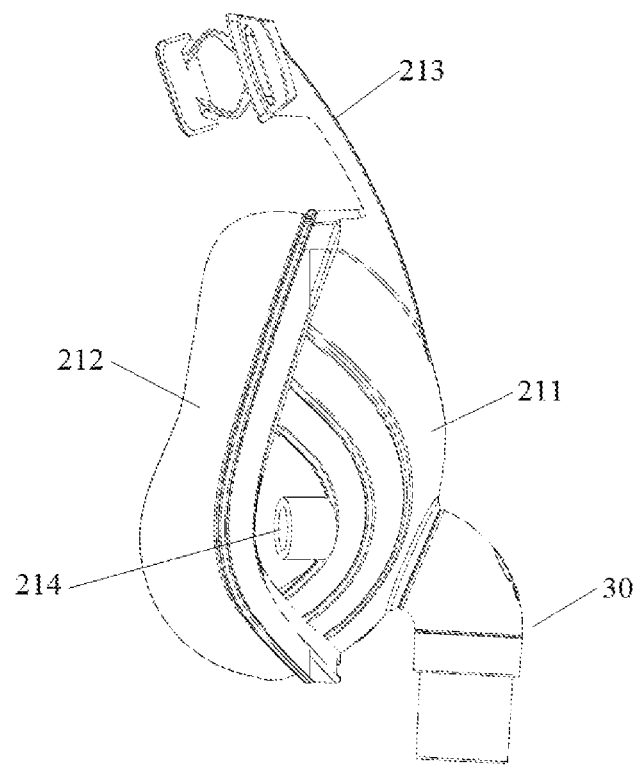
FIG. 7 is a schematic diagram of the connection of the main body of the patient-interface device and the tube assembly in FIG. 1.

In addition, as shown in FIG. 7, the ventilation-treatment apparatus may further include a tube assembly 30, and the tube assembly 30 is connected to the main body 21 to communicate the respiratory cavity with the gas source. Particularly, one end of the tube assembly 30 may be connected to the frame 211, and the other end may be connected to the ventilation pipeline 50. In this case, the ventilation-treatment apparatus may adopt two modes of the ventilation, wherein one is to ventilate by using the headrest 10 and the head band 22, and the other is to ventilate by using the tube assembly 30. In usage, a suitable ventilation mode may be selected according to actual situations. It should be noted that, when the ventilation by using the headrest 10 and the head band 22 is adopted, the tube assembly 30 and the ventilation pipeline 50 may be disconnected, and the tube assembly 30 may be blocked by using a plug. Certainly, optionally, the tube assembly 30 may also be taken down from the frame 211, and the opening for connecting the tube assembly 30 on the frame 211 is blocked by using a plug. When the ventilation by using the tube assembly 30 is adopted, optionally, the first valve assembly is disposed at one of the tube assembly 30 and the ventilation pipeline 50, and the second valve assembly is disposed at the other of the tube assembly 30 and the ventilation pipeline 50. In usage, when the tube assembly 30 and the ventilation pipeline 50 are connected, the first gas hole 12 and the second gas hole 222 are opened, and when the tube assembly 30 and the ventilation pipeline 50 are disconnected, the first gas hole 12 and the second gas hole 222 are closed.

In the usage of current ventilation-treatment apparatuses, when the patient intends to pause the treatment and thus directly disengages the breathing mask from the ventilation pipeline, because the mainframe is still in the operating state, that results in a large gas-leakage noise at the port of the ventilation pipeline, and a device alarming might be triggered because of a too large gas-leakage amount. In order to solve the above problems, the present disclosure provides a novel tube assembly 30. The tube assembly 30 may include a first tube piece 31 and a second tube piece 32, the tube assembly 30 has a connecting state in which the first tube piece 31 and the second tube piece 32 are coaxially plug-connected and a separating state in which the first tube piece 31 and the second tube piece 32 are separate from each other, and the first tube piece 31 has an inlet end for connecting the gas source and an outlet end for connecting the second tube piece 32; the first tube piece 31 has a discharging hole 311, and the discharging hole 311 is configured so that, in the connecting state, the discharging hole 311 is closed to make the gas from the gas source to enter the second tube piece 32, and in the separating state, the discharging hole 311 is opened to make the gas from the gas source to be discharged from the discharging hole 311 to the external; and the tube assembly 30 further includes a valve member, and the valve member is configured so that, in the connecting state, the valve member opens the outlet end of the first tube piece 31 to make the gas from the gas source to enter the second tube piece 32, and in the separating state, the valve member closes the outlet end to make the gas from the gas source to be discharged from the discharging hole 311 to the external.

In the above description, it should be noted that the hole area of the discharging hole 311 is less than the area of the outlet end of the first tube piece 31; in other words, the ventilation capacity of the discharging hole 311 is less than the ventilation capacity of the outlet end. In usage, by configuring the hole diameter and the quantity of the discharging hole 311, the flow rate of the gas discharged from the discharging hole 311 may be controlled, whereby, when the first tube piece 31 and the second tube piece 32 are separate from each other, the gas cannot flow out of the outlet end of the first tube piece 31, and may merely flow out of the discharging hole 311 at a desired lower flow rate.

In usage, when the patient intends to pause the treatment (for example, getting up and going to the bathroom), it is merely required to separate the first tube piece 31 and the second tube piece 32. At this point, the outlet end of the first tube piece 31 is closed, the discharging hole 311 is opened, the first tube piece 31 discharges the gas at a controllable flow rate, and the ventilation-treatment apparatus may operate normally and does not make an alarm due to gas leakage or pipeline falling, whereby the bed partner is not disturbed. Furthermore, the ventilation-treatment apparatus may be used and stopped at any time, and does not influence other actions of the patient, with easy and convenient operation and usage, and good safety and sanitary.

In the tube assembly 30 according to the present disclosure, by using the above technical solutions, when the first tube piece 31 and the second tube piece 32 are plug-connected to each other, the valve member opens the outlet end of the first tube piece 31 to allow the gas to flow from the first tube piece 31 to the second tube piece 32, and the discharging hole 311 is closed to prevent the gas from flowing out of the discharging hole 311 at the same time, whereby the gas may merely flow from the first tube piece 31 to the second tube piece 32. When the first tube piece 31 and the second tube piece 32 are separate from each other, the valve member closes the outlet end of the first tube piece 31 to prevent the gas from flowing out of the outlet end, and simultaneously the discharging hole 311 is opened to make the gas to be discharged from the discharging hole 311 to the external at a lower flow rate. Accordingly, the tube assembly according to the present disclosure cannot only ensure the effective flowing of the gas, but also, when the first tube piece 31 and the second tube piece 32 are separate from each other, may enable the gas to be discharged to the external at a lower flow rate, thereby preventing the generation of gas-leakage noise.

Figure 10:
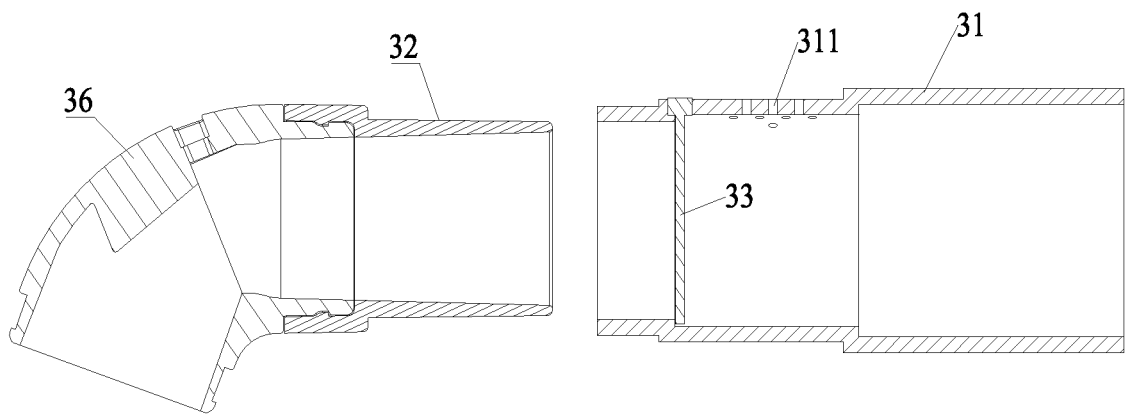
FIG. 10 is a sectional view of the first embodiment of the tube assembly according to the present disclosure, wherein the tube assembly is in the separating state.
Figure 11:
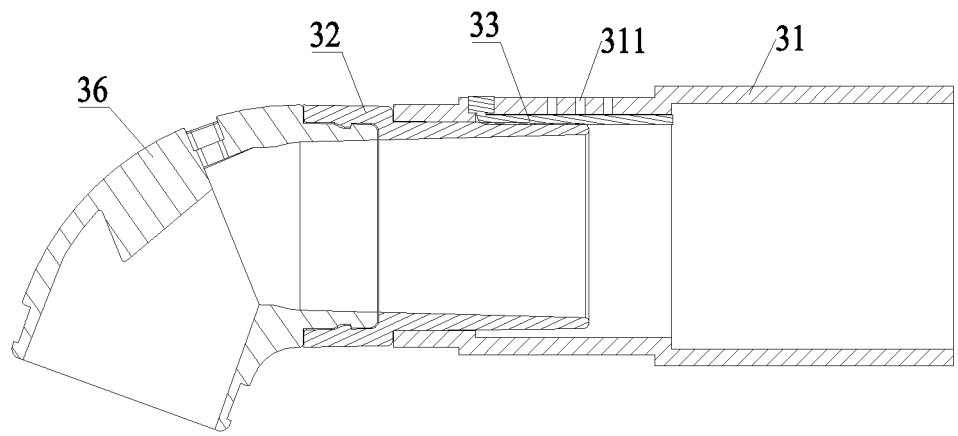
FIG. 11 is a schematic diagram of the connecting state of the tube assembly in FIG. 10.
Figure 12:
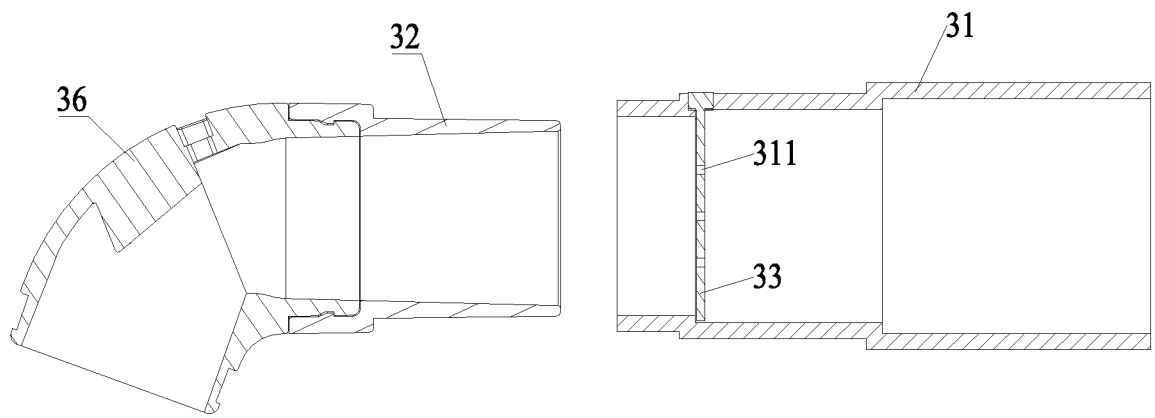
FIG. 12 is a sectional view of the second embodiment of the tube assembly according to the present disclosure, wherein the tube assembly is in the separating state.
Figure 14:
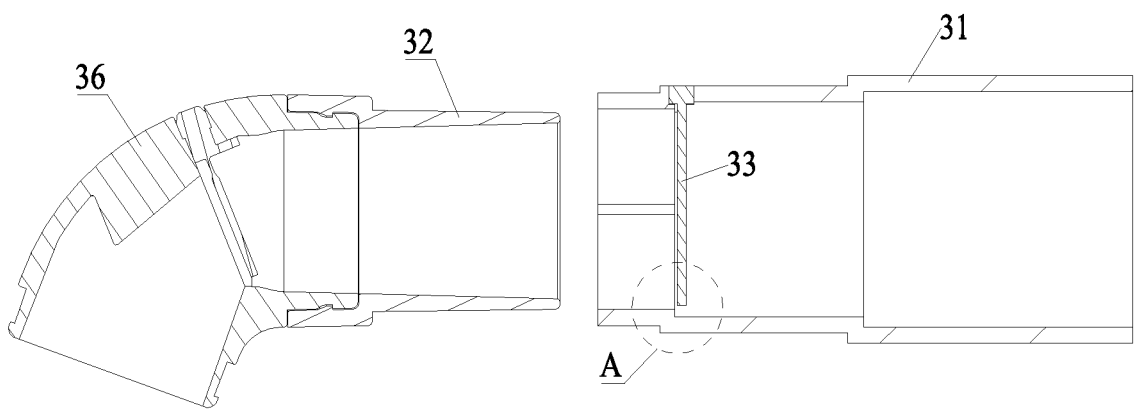
FIG. 14 is a sectional view of the fourth embodiment of the tube assembly according to the present disclosure, wherein the tube assembly is in the separating state.
Figure 15:
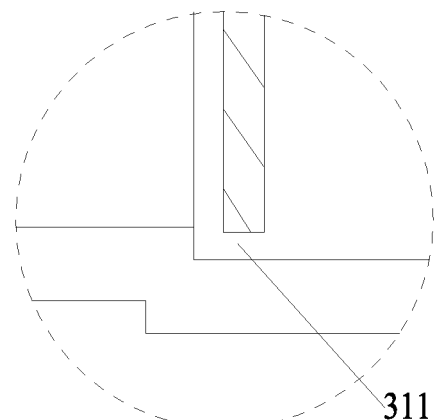
FIG. 15 is an enlarged view of the part A in FIG. 14.
Figure 16:
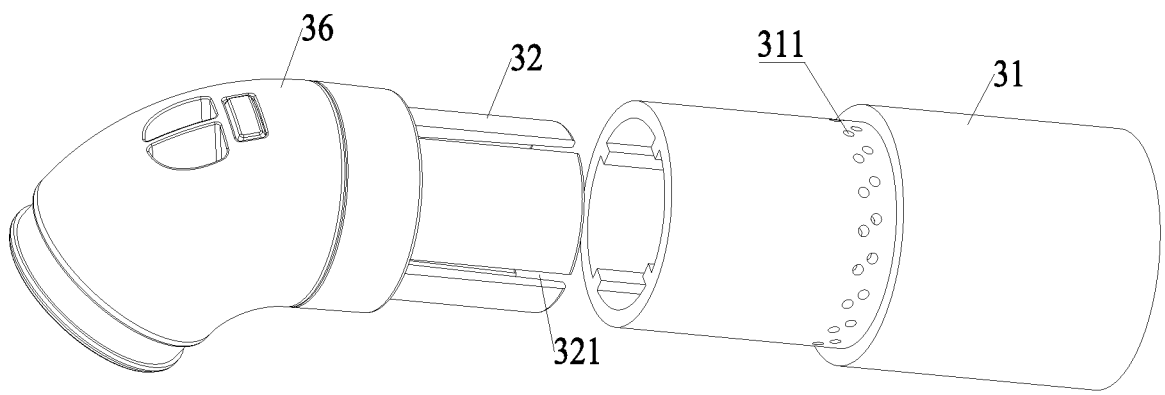
FIG. 16 is a schematic structural diagram of the fifth embodiment of the tube assembly according to the present disclosure, wherein the tube assembly is in the separating state.

According to an embodiment of the valve member according to the present disclosure, the valve member includes a valve plate 33 rotatably disposed inside the first tube piece 31, the rotation axis of the valve plate 33 is perpendicular to the axial direction of the first tube piece 31, and the valve plate 33 may rotate between a first position where the discharging hole 311 is closed and the outlet end of the first tube piece 31 is opened (referring to FIG. 11) and a second position where the discharging hole 311 is opened and the outlet end of the first tube piece 31 is closed (referring to FIG. 10). In this case, the valve plate 33 may be configured in two different modes. One is to configure the valve plate 33 so that, in the second position, the edge of the valve plate 33 abuts the inner wall surface of the first tube piece 31; in other words, the valve plate 33 may completely block the outlet end. In this case, the discharging hole 311 may be disposed in the tube wall of the first tube piece 31 (as shown in FIGS. 10 and 11), and may also be disposed in the valve plate 33 (as shown in FIG. 12). The other mode is to configure the valve plate 33 so that, in the second position, the edge of the valve plate 33 and the inner wall surface of the first tube piece 31 have a gap therebetween, and the gap forms the discharging hole 311 (as shown in FIGS. 14 and 15).

Figure 13:
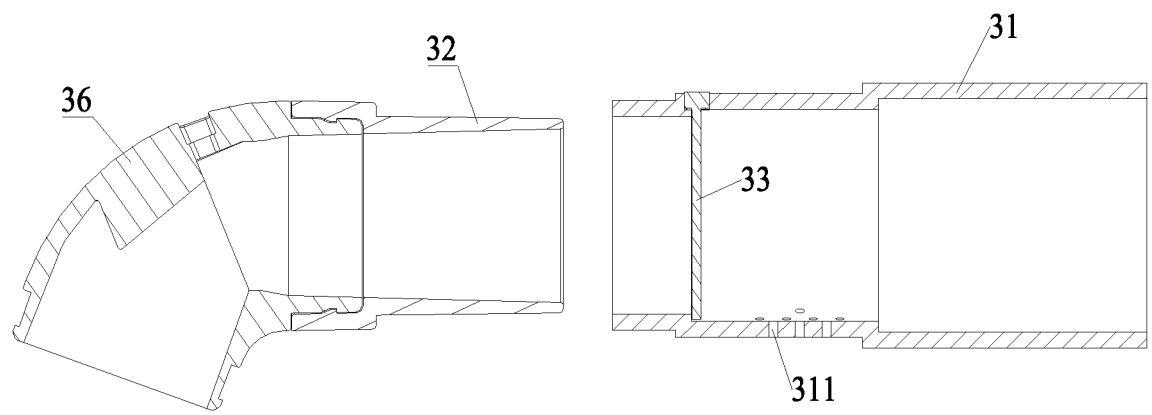
FIG. 13 is a sectional view of the third embodiment of the tube assembly according to the present disclosure, wherein the tube assembly is in the separating state.

In other words, in the above modes, both of the opening and closing of the discharging hole 311 and the opening and closing of the outlet end of the first tube piece 31 are implemented by using the valve plate 33. Certainly, according to the different positions of the discharging hole 311 in the tube wall of the first tube piece 31, the valve plate 33 may also cooperate with the second tube piece 32 to implement the function of the valve member. As shown in FIG. 13, the valve plate 33 is connected to the top of the tube wall of the first tube piece 31, and the discharging hole 311 is disposed at the bottom of the tube wall of the first tube piece 31. In this case, when the second tube piece 32 is inserted into the first tube piece 31, the second tube piece 32 pushes the valve plate 33 to the first position to open the outlet end of the first tube piece 31, and simultaneously the tube wall of the second tube piece 32 blocks the discharging hole 311. It should be noted that, after the second tube piece 32 has been inserted into the first tube piece 31, the outer wall surface of the second tube piece 32 is closely adhered to the side surface of the valve plate 33 and the inner wall surface of the first tube piece 31, to prevent gas leakage.

According to another embodiment of the valve member according to the present disclosure, as shown in FIGS. 16 to 20, the valve member includes a valve core 34 that is movably disposed inside the first tube piece 31 in the axial direction of the first tube piece 31, the discharging hole 311 is disposed in the tube wall of the first tube piece 31, and the second tube piece 32 is disposed with a gas flowing channel 321. The tube assembly 30 is configured so that, in the connecting state, the valve core 34 moves to the upstream position of the discharging hole 311 in the direction of the gas flowing (i.e., the direction from the first tube piece 31 to the second tube piece 32), the part of the second tube piece 32 that protrudes into the first tube piece 31 forms, together with the valve core 34, the valve member to close the discharging hole 311, and the first tube piece 31 communicates with the second tube piece 32 via the gas flowing channel 321 (referring to FIGS. 18 and 20); and in the separating state, the valve core 34 moves to the downstream position of the discharging hole 311 in the direction of the gas flowing to close the outlet end of the first tube piece 31 (referring to FIGS. 17 and 19).

Figure 17:
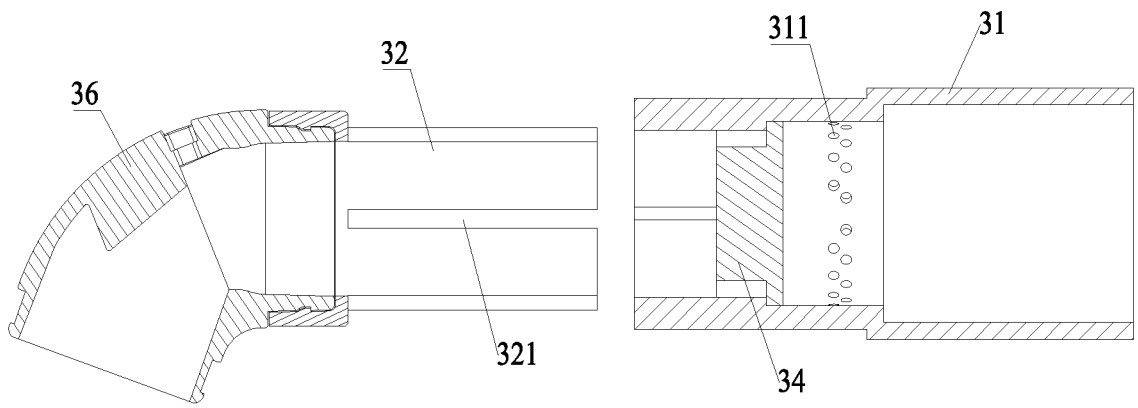
FIG. 17 is a sectional view of FIG. 16.
Figure 18:
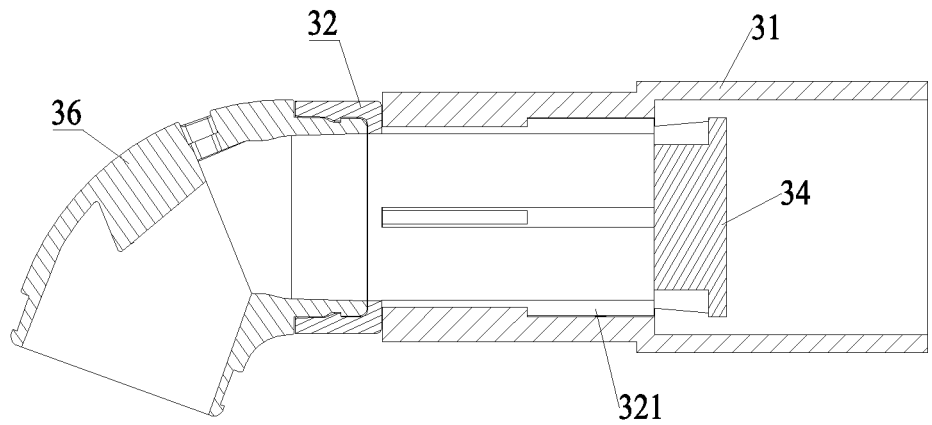
FIG. 18 is a schematic diagram of the connecting state of the tube assembly in FIG. 17.
Figure 19:
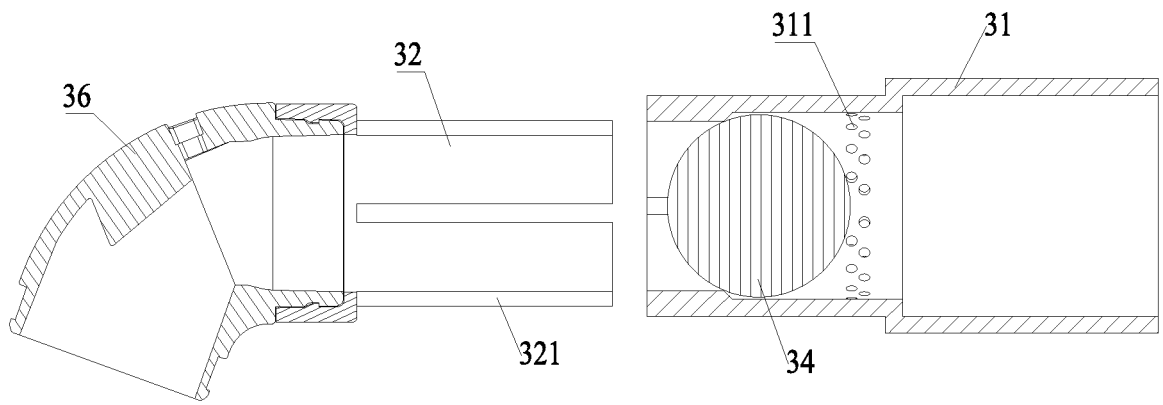
FIG. 19 is a sectional view of the sixth embodiment of the tube assembly according to the present disclosure, wherein the tube assembly is in the separating state.
Figure 20:
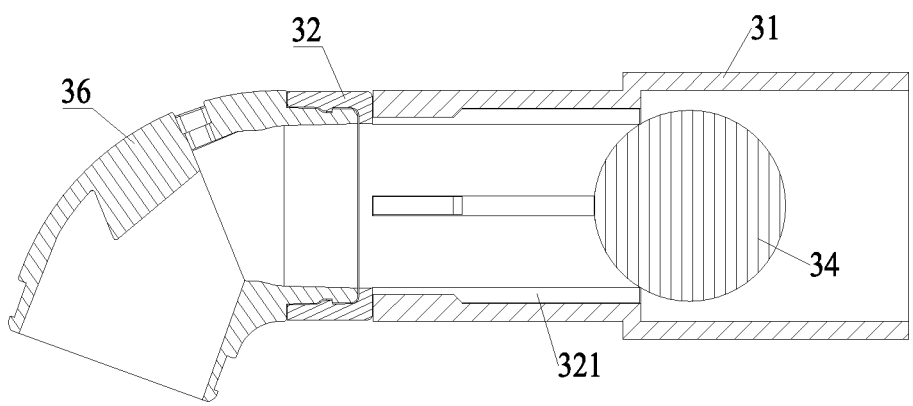
FIG. 20 is a schematic diagram of the connecting state of the tube assembly in FIG. 19.

In the above description, the valve core 34 may be any component that is capable of moving inside the first tube piece 31 and capable of blocking the outlet end of the first tube piece 31; for example, the valve core 34 may be a cylindrical body or a spherical body. In usage, for example, as shown in FIGS. 17 and 18, when the second tube piece 32 is inserted into the first tube piece 31, the second tube piece 32 may push the valve core 34, which is originally located at the second position (referring to FIG. 17), to move rightwardly to the first position (referring to FIG. 18), at which point the discharging hole 311 is covered by the tube wall of the second tube piece 32 and thus closed, and the gas inside the first tube piece 31 enters the second tube piece 32 via the gap between the valve core 34 and the inner wall surface of the first tube piece 31 and the gas flowing channel 321. When the second tube piece 32 and the first tube piece 31 are separate, the valve core 34 moves, by the effect of the mobilization force of the gas, from the first position back to the second position, thereby blocking the outlet end, to make the gas to be discharged via the discharging hole 311.

It may be understood that, in order to enable the valve core 34 to block the outlet end at the second position and generate the gap with the inner wall surface of the first tube piece 31 when the valve core 34 moves to the first position, while the first tube piece 31 is configured to be of a non-constant-diameter structure, as shown in FIGS. 17 to 20.

Figure 21:
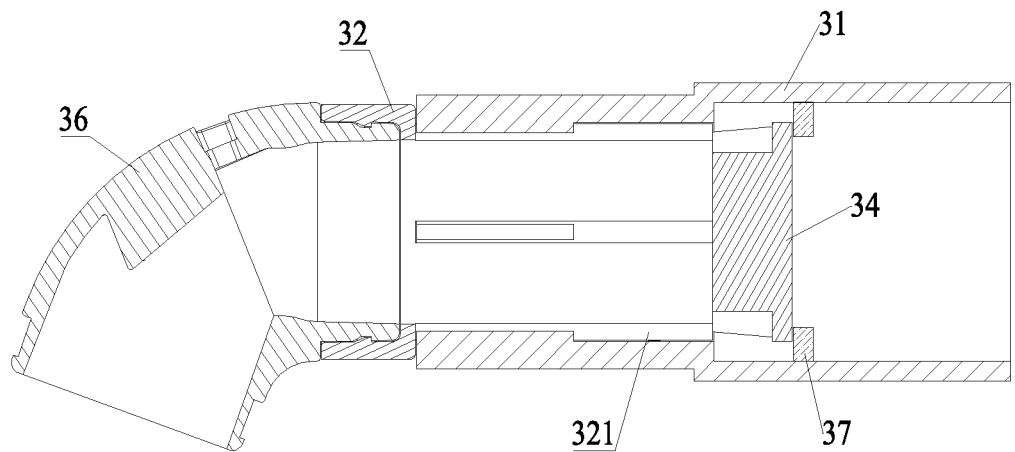
FIG. 21 is a schematic diagram in which the tube assembly in FIG. 18 is disposed with a valve-core stopper.
Figure 22:
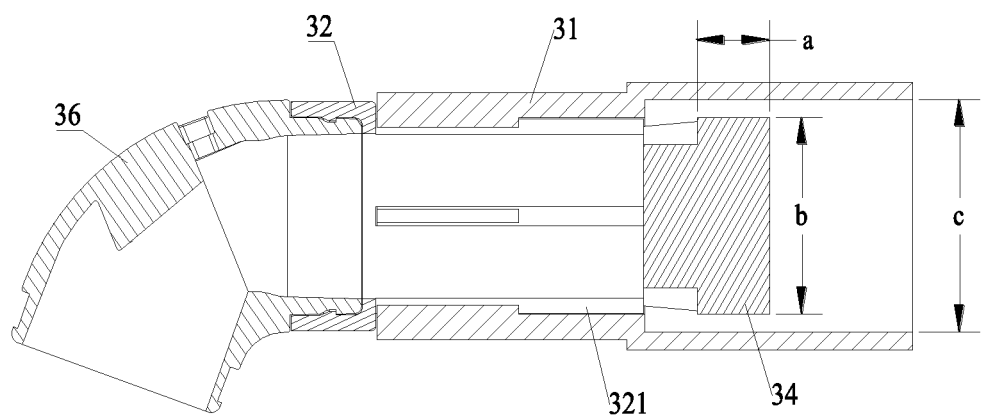
FIG. 22 is a schematic diagram in which the tube assembly in FIG. 18 is disposed with a valve cores of different structures.

In order to prevent the valve core 34 from, in the first position, continuing to move rightwardly or turning over, to affect the usage of the valve core 34 or even make failure of the device, the valve member may further include a valve-core stopper 37 disposed inside the first tube piece 31, and the valve-core stopper 37 is configured so that it may limit the valve core 34. Particularly, for example, as shown in FIG. 21, the valve-core stopper 37 may be an annular boss disposed on the inner wall of the first tube piece 31, and when the valve core 34 is in the first position, the right side surface of the valve core 34 is capable of abutting the left side surface of the annular boss, whereby the valve core 34 cannot continue to move rightwardly, and cannot turn over. Certainly, the right side surface of the valve core 34 may also have a gap with the left side surface of the annular boss, wherein the gap is less than the axial length of the valve core 34, which may prevent turning-over of the valve core 34 in the horizontal direction (i.e., left-right turning-over). Optionally, the gap between the right side surface of the valve core 34 and the left side surface of the annular boss is preferably set to be less than the maximum diameter of the valve core 34, which may prevent turning-over of the valve core 34 in the vertical direction (i.e., up-down turning-over). In addition, for example, as shown in FIG. 22, the valve core 34 may also be made to be more stable itself in structure. As compared with the valve core 34 in FIG. 21, the center of gravity of the valve core 34 in FIG. 22 is deviated to right, which may improve the stability of the valve core 34 in the first position. Optionally, referring to FIG. 22, the magnitude of a may be between one third and two thirds of c, or $a^2+b^2=c^2$, which may prevent turning-over of the valve core 34. Certainly, the present disclosure is not limited thereto, and the valve-core stopper 37 may be any component or structure that may limit the valve core 34 as described above.

In the present disclosure, when the tube assembly 30 is in the connecting state, the first tube piece 31 and the second tube piece 32 may be configured to be capable of rotating relatively to each other, and may also be configured to be not capable of rotating. In addition, the tube assembly 30 may further include a connecting structure for connecting the first tube piece 31 and the second tube piece 32, and the connecting structure is configured to be capable of preventing the first tube piece 31 and the second tube piece 32 from separating from each other in the connecting state. That may prevent the first tube piece 31 and the second tube piece 32 from being separated accidentally to affect the gas flowing.

According to an embodiment of the connecting structure according to the present disclosure, the connecting structure includes a clip 312 and a clipping slot 322 that match, the clip 312 is disposed at one of the first tube piece 31 and the second tube piece 32, and the clipping slot 322 is disposed at the other of the first tube piece 31 and the second tube piece 32.

Figure 23:
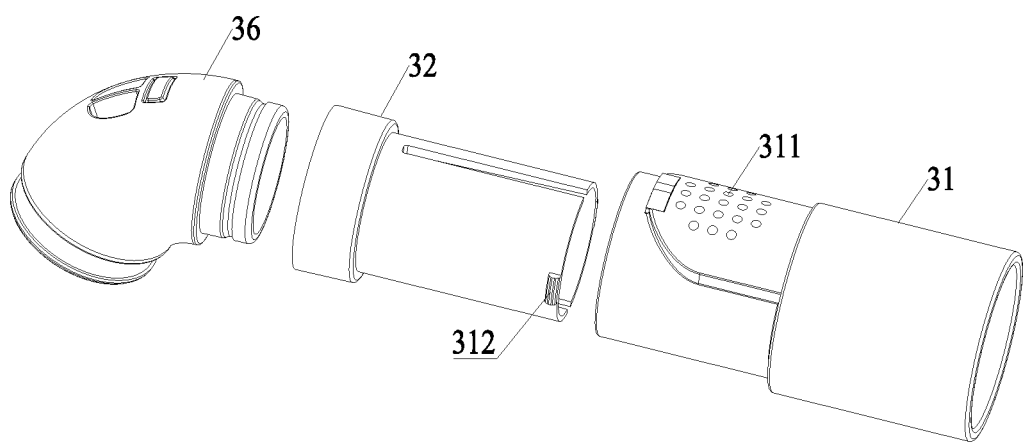
FIG. 23 is a schematic diagram in which the connecting structure according to the first embodiment of the present disclosure is disposed at the tube assembly, wherein the tube assembly is in the separating state.
Figure 24:
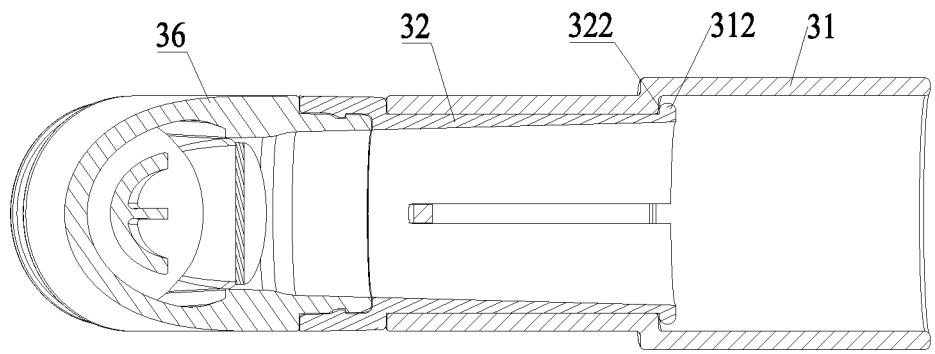
FIG. 24 is a sectional view of the connecting state of the tube assembly in FIG. 23.

In the above embodiment, the clip 312 and the clipping slot 322 may be configured in various modes. For example, as shown in FIGS. 23 and 24, the clip 312 may be disposed on the outer wall surface of the second tube piece 32, and the clipping slot 322 may be disposed on the inner wall surface of the first tube piece 31, wherein when it is required to separate the first tube piece 31 and the second tube piece 32, the clip 312 and the clipping slot 322 may be separated by using a heavy force.

Figure 25:
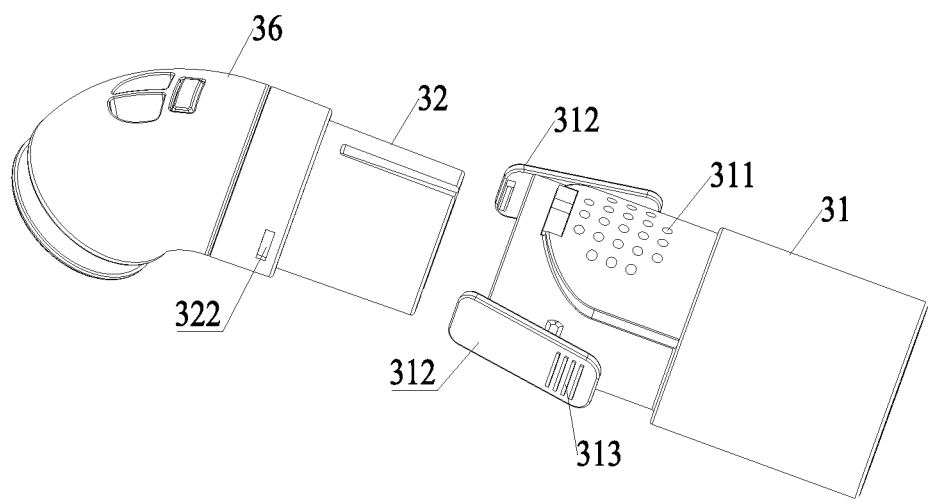
FIG. 25 is a schematic diagram in which the connecting structure according to the second embodiment of the present disclosure is disposed at the tube assembly, wherein the tube assembly is in the separating state.
Figure 26:
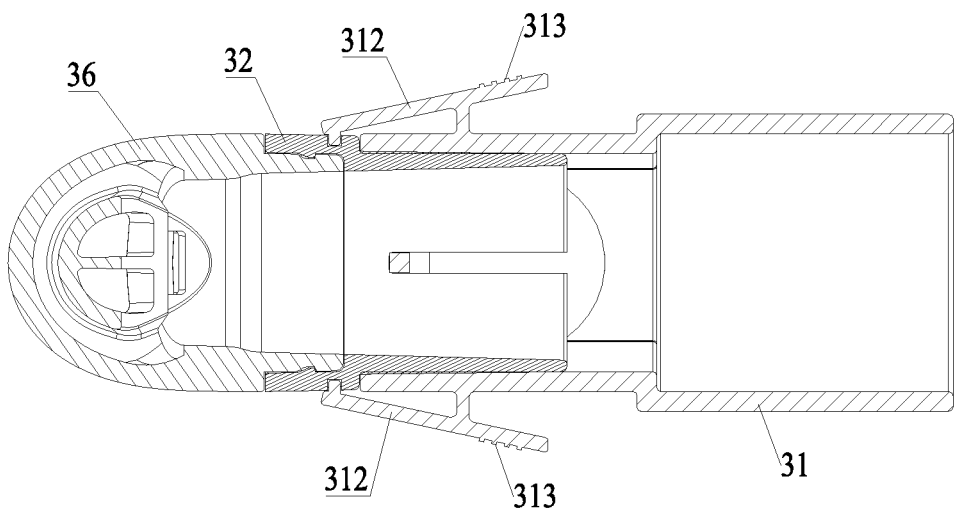
FIG. 26 is a sectional view of the connecting state of the tube assembly in FIG. 25.

For example, as shown in FIGS. 25 and 26, the clipping slot 322 may be disposed on the outer wall surface of the second tube piece 32, the clip 312 may be rotatably connected to the outer wall surface of the first tube piece 31, and the clip 312 is configured to be capable of swinging in the radial direction of the first tube piece 31 to be snap-fitted to or separated from the clipping slot 322. The clipping slot 322 may be of an arc shape or annular shape that extends in the circumferential direction of the second tube piece 32, and its length of extension is greater than the corresponding length of its snap fitting to the clip 312; in this case, one clipping slot 322 may be snap-fitted to a plurality of clips 312. In addition, in such a mode of configuration, in order to prevent the clip 312 from disengaging from the clipping slot 322 when it is snap-fitted to the clipping slot 322, the clip 312 may be configured to have a snap-fitting state in which it is snap-fitted to the clipping slot 322 and a separating state in which it is separated from the clipping slot 322. Furthermore, the clip 312 swings from the snap-fitting state to the separating state merely when it is applied a force, and the clip 312 is always in the snap-fitting state naturally. As shown in FIG. 25, when it is required to snap-fit the clip 312 to the clipping slot 322, the right end of the clip 312 may be pressed to firstly make the clip 312 to swing to the separating state to allow it to be snap-fitted to the clipping slot 322. A slide-proof part 313 may be disposed on the outer side surface of the right end of the clip 312.

Figure 27:
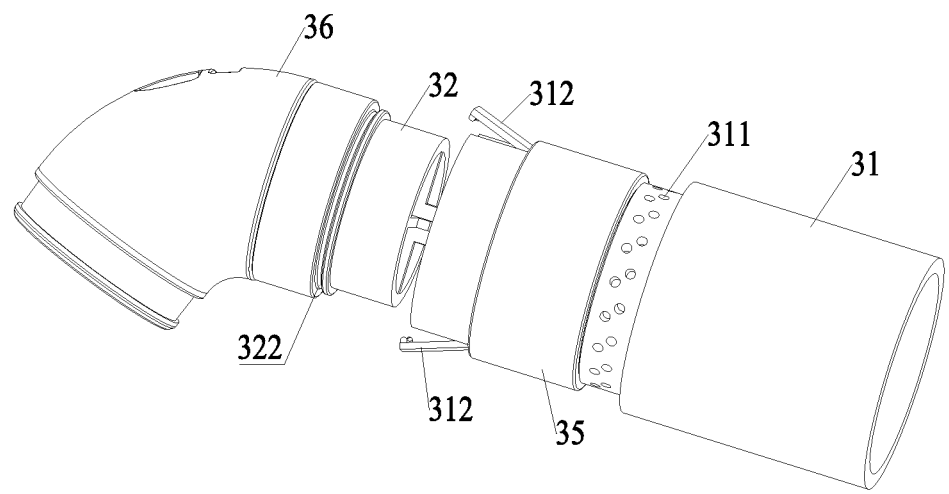
FIG. 27 is a schematic diagram in which the connecting structure according to the third embodiment of the present disclosure is disposed at the tube assembly, wherein the tube assembly is in the separating state, and a lantern ring is nested outside the first tube piece.
Figure 28:
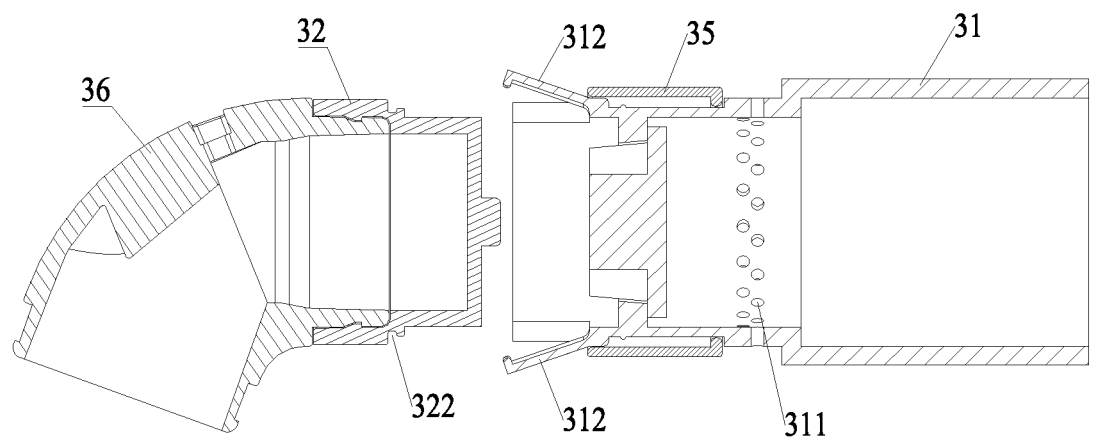
FIG. 28 is a sectional view of FIG. 27.
Figure 29:
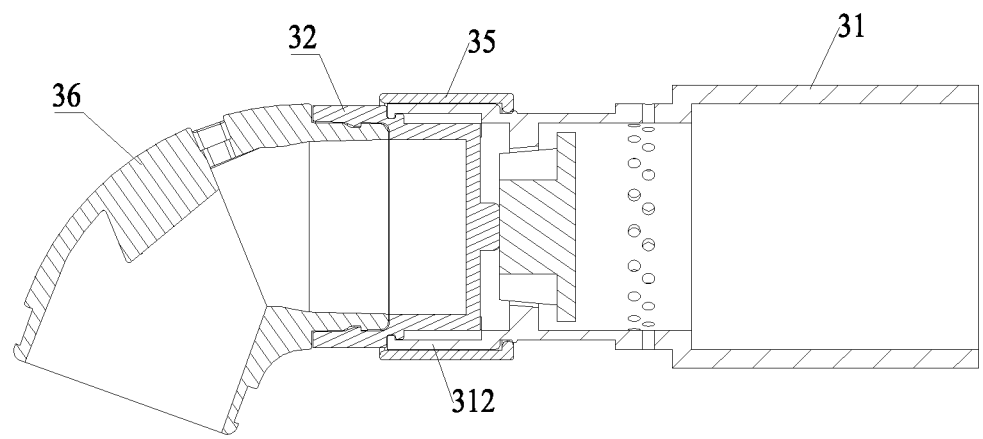
FIG. 29 is a schematic diagram of the connecting state of the tube assembly in FIG. 28.

Certainly, another component may also be used to prevent the clip 312 from disengaging from the clipping slot 322 when it is snap-fitted to the clipping slot 322. In other words, the tube assembly 30 may include a limiting member, and the limiting member is for preventing the clip 312 from disengaging from the clipping slot 322 when it is snap-fitted to the clipping slot 322. For example, as shown in FIGS. 27 to 29, the limiting member is a lantern ring 35 that is movably nested outside the first tube piece 31 or the second tube piece 32 in the axial direction of the first tube piece 31. When the clip 312 is snap-fitted to the clipping slot 322, the lantern ring 35 may be moved leftwardly to cover the clip 312, thereby preventing the clip 312 from rotating. When it is required to separate the first tube piece 31 and the second tube piece 32, firstly the lantern ring 35 is moved rightwardly to expose the clip 312, and subsequently the clip 312 is rotated till it is separated from the clipping slot 322.

Figure 30:
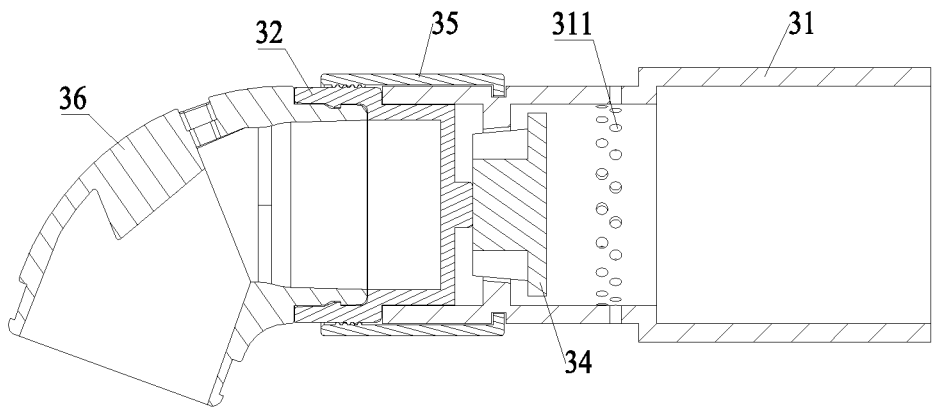
FIG. 30 is a sectional view in which the connecting structure according to the fourth embodiment of the present disclosure is disposed at the tube assembly, wherein the tube assembly is in the connecting state.

It may be envisaged that, in another embodiment, as shown in FIG. 30, the connecting structure may also merely include the lantern ring 35, the lantern ring 35 is rotatably connected to the first tube piece 31, and the inner wall surface of the lantern ring 35 may be disposed with an internal thread. Correspondingly, the outer wall surface of the second tube piece 32 may be disposed with an external thread, and the internal thread and the external thread may be mutually locked by rotating the lantern ring 35, whereby the first tube piece 31 and the second tube piece 32 are connected. When it is required to separate the first tube piece 31 and the second tube piece 32, the lantern ring 35 may be rotated in the opposite direction, whereby the threads are released, to complete the separation.

Figure 31:
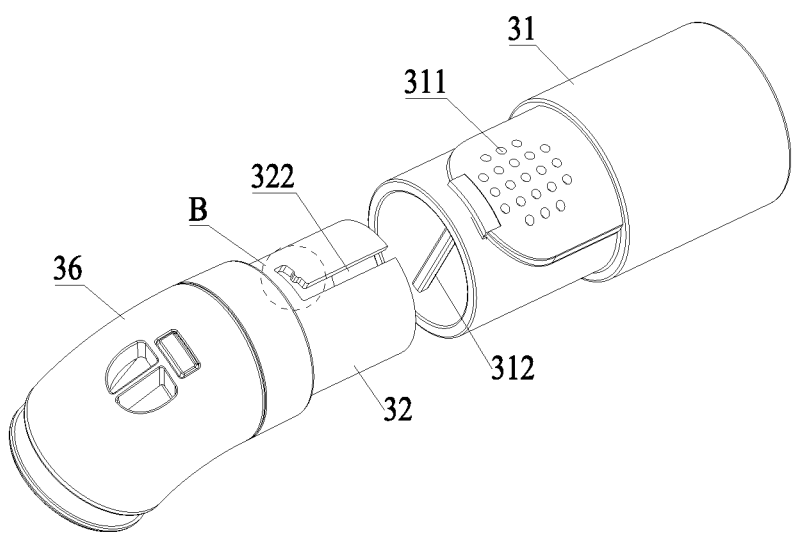
FIG. 31 is a schematic diagram in which the connecting structure according to the fifth embodiment of the present disclosure is disposed at the tube assembly, wherein the tube assembly is in the separating state.
Figure 32:
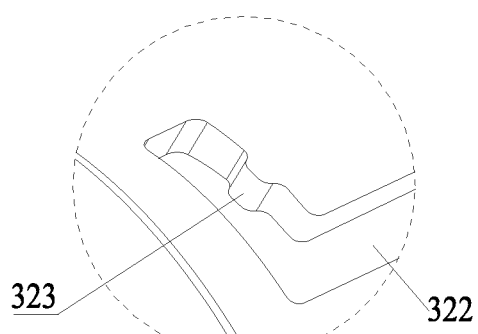
FIG. 32 is an enlarged view of the part B in FIG. 31.
Figure 33:
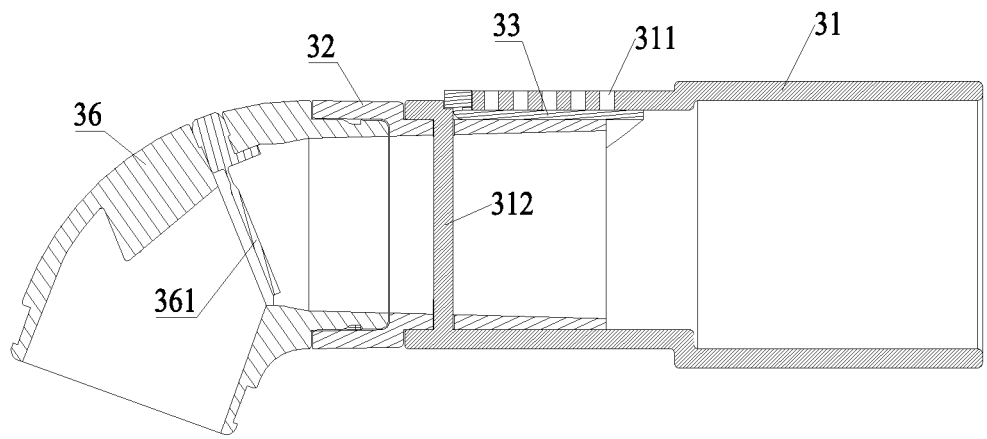
FIG. 33 is a sectional view of the connecting state of the tube assembly in FIG. 31.

For example, as shown in FIGS. 31 to 33, the clipping slot 322 is an L-shaped slot disposed in the tube wall of the second tube piece 32, the L-shaped slot includes an axial part and a radial part, the clip 312 is a cylindrical piece that is protrusively disposed on the tube wall of the first tube piece 31, and the cylindrical piece is capable of, when the first tube piece 31 and the second tube piece 32 are plug-connected, entering the axial part and moving to the radial part to implement the snap fitting. In this case, in order to prevent the clip 312 from disengaging from the clipping slot 322 when it is snap-fitted to the clipping slot 322, as shown in FIG. 32, the limiting member may be a lug 323 disposed inside the radial part, and the lug 323 may releasably stop the cylindrical piece. In usage, by rotating the first tube piece 31 or the second tube piece 32, the cylindrical piece may move over the lug 323 and move to the left side of the lug 323 to implement the limiting. When it is required to separate the first tube piece 31 and the second tube piece 32, the first tube piece 31 or the second tube piece 32 may be rotated in the opposite direction, whereby the cylindrical piece moves over the lug 323 and moves to the right side of the lug 323, and in turn disengages the clipping slot 322.

It should be noted that, in the above description, the clip 312 and the clipping slot 322 may exchange the positions. In addition, the clip 312 and the clipping slot 322 are not limited to the above-described structures, and other structures that may implement their function also fall within the protection scope of the present disclosure.

Figure 34:
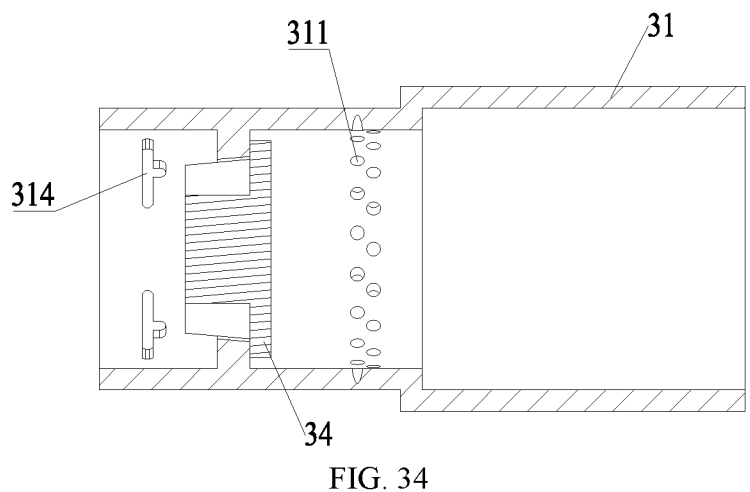
FIG. 34 is a schematic diagram in which the first protrusion of the connecting structure according to the sixth embodiment of the present disclosure is disposed at the first tube piece.
Figure 35:
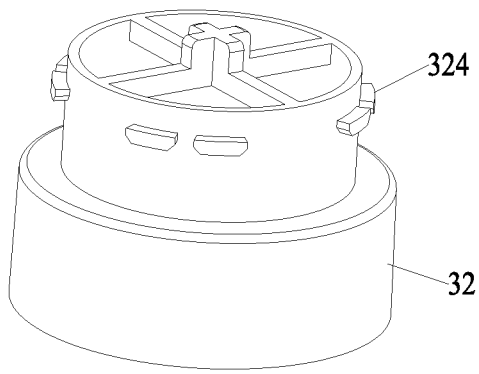
FIG. 35 is a schematic diagram in which the second protrusion of the connecting structure according to the sixth embodiment of the present disclosure is disposed at the second tube piece.
Figure 36:
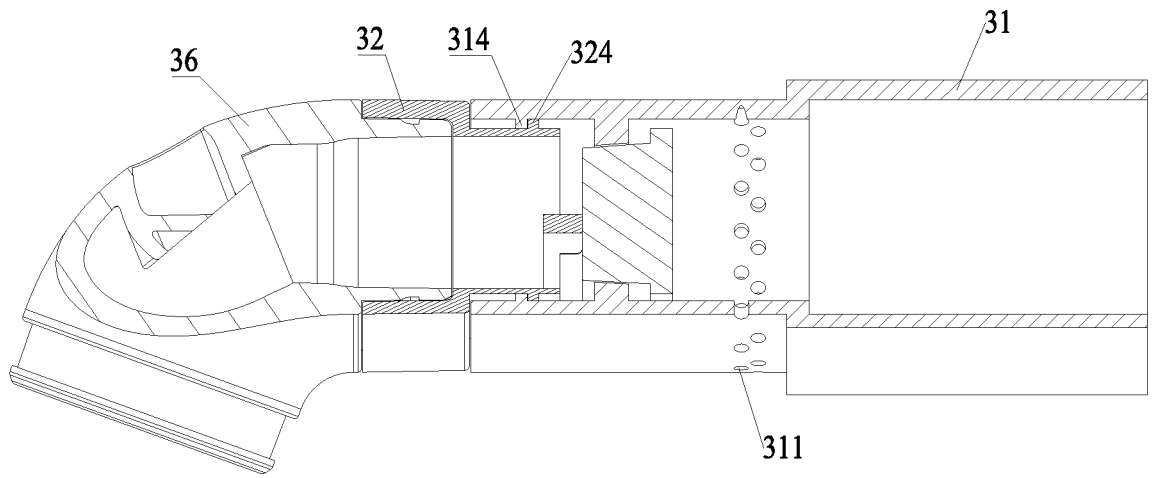
FIG. 36 is a sectional view in which the first tube piece in FIG. 34 and the second tube piece in FIG. 35 are connected, wherein the second tube piece is connected to a bent pipe at the end that is further from the first tube piece.
Figure 37:
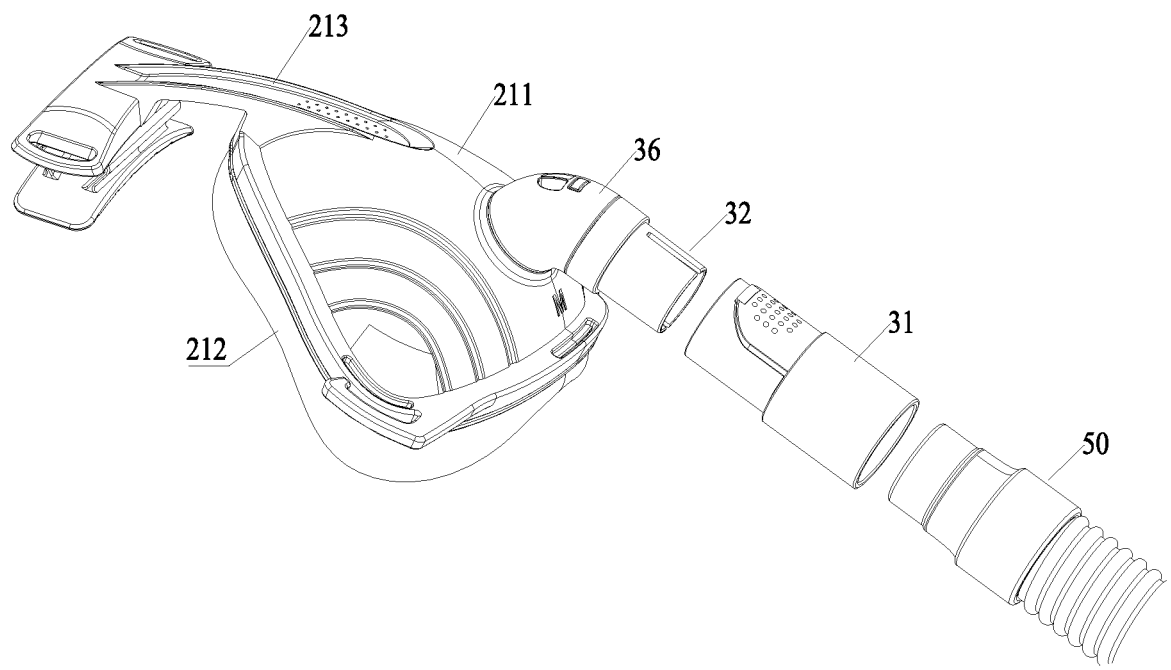
FIG. 37 is a schematic diagram of the assembling between the tube assembly according to the present disclosure with a breathing mask and a ventilation pipeline.
Figure 38:
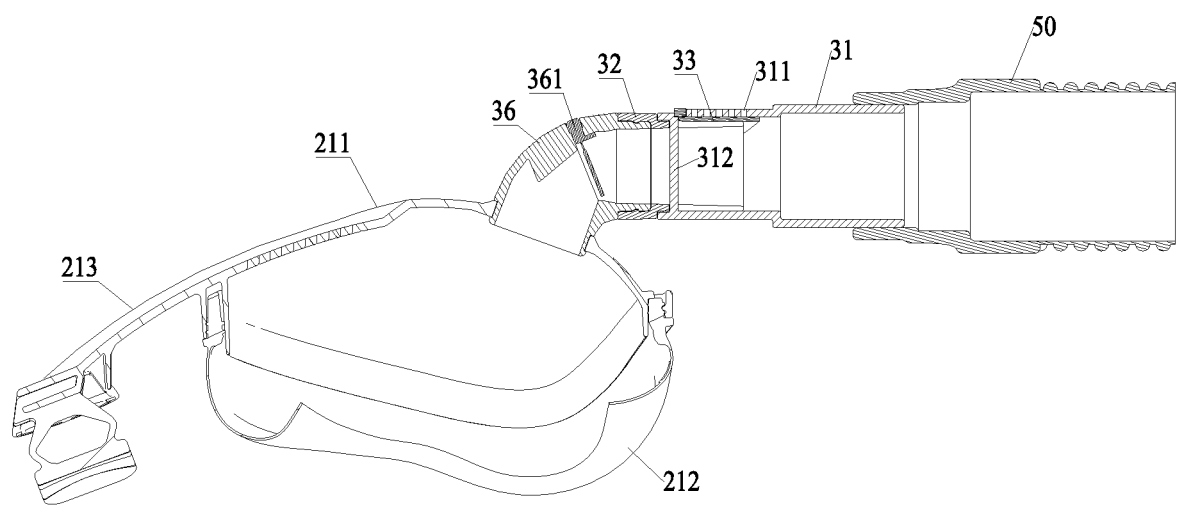
FIG. 38 is a sectional view in which the tube assembly in FIG. 37 is connected to the breathing mask and the ventilation pipeline.

According to another embodiment of the connecting structure according to the present disclosure, as shown in FIGS. 34 to 36, the connecting structure includes a first protrusion 314 and a second protrusion 324 that match, the first protrusion 314 is disposed on the inner wall surface or the outer wall surface of the first tube piece 31, the second protrusion 324 is disposed on the outer wall surface or the inner wall surface of the second tube piece 10, and the first protrusion 314 and the second protrusion 324 are configured to be capable of snap-fitting or separating by the rotation relative to each other of the first tube piece 31 and the second tube piece 32. Particularly, as shown in FIG. 34, the first protrusion 314 may be T-shaped. As shown in FIG. 35, the second protrusion 324 may include two convex parts that are separated in the circumferential direction of the second tube piece 32. When the second tube piece 32 is plug-connected to the first tube piece 31, the first protrusion 314 and the second protrusion 324 are made to avoid each other, and after the plug connection, by rotating the first tube piece 31 or the second tube piece 32, the first protrusion 314 and the second protrusion 324 may face each other axially to implement the snap fitting, at which point the axial part of the first protrusion 314 is snap-fitted between the two convex parts to implement the rotary limiting. Certainly, the first protrusion 314 and the second protrusion 324 are not limited to the structures shown in FIGS. 34 and 35, and other structures that may implement the rotary snap fitting also fall within the protection scope of the present disclosure.

It should be noted that, in the above-described embodiments of the connecting structure, the connecting structure may include a plurality of clips 312 and a plurality of clipping slots 322. The plurality of clips 312 and the plurality of clipping slots 322 may be disposed separately in the circumferential directions of the first tube piece 31 and the second tube piece 32, respectively.

According to yet another embodiment of the connecting structure according to the present disclosure, the connecting structure may include a first magnet and a second magnet which magnetic poles are opposite, the first magnet is set at one of the first tube piece 31 and the second tube piece 32, and the second magnet is set at the other of the first tube piece 31 and the second tube piece 32. After the first tube piece 31 and the second tube piece 32 have been plug-connected, further connection may be implemented by the attraction between the first magnet and the second magnet.

According to still another embodiment of the connecting structure according to the present disclosure, the connecting structure may include a first thread and a second thread that match, the first thread is disposed at one of the first tube piece 31 and the second tube piece 32, and the second thread is disposed at the other of the first tube piece 31 and the second tube piece 32. In other words, the first tube piece 31 and the second tube piece 32 may be interconnected by the threads disposed on the inner wall surfaces or the outer wall surfaces.

The connecting structure according to the present disclosure is not limited to the above-described embodiments, and the connecting structure may also have other embodiments. For example, the second tube piece 32 may be disposed with a metal that may be magnetically attracted (for example, iron), and the first tube piece 31 may be disposed with an electromagnet device and a switch. Alternatively, the first tube piece 31 and the second tube piece 32 are disposed with an electric buckle and a buckle slot that match. When the second tube piece 32 is inserted into the first tube piece 31, the switch is closed to form a loop, and the electromagnet, when electrified, has magnetism, to attract the metal on the second tube piece 32, whereby the first tube piece 31 and the second tube piece 32 do not easily disengage. Alternatively, after the loop has been formed, the electric buckle acts to buckle the buckle slot in the second tube piece 32. When the first tube piece 31 and the second tube piece 32 are to be separated, the switch is operated, and the electromagnet, when powered off, loses the magnetism, or the electric buckle, when powered off, is restored, whereby the first tube piece 31 and the second tube piece 32 may be easily separated.

In the present disclosure, the tube assembly 30 may further include a bent pipe 36, and the bent pipe 36 is connected to the end of the second tube piece 32 that is further from the first tube piece 31. The bent pipe 36 and the second tube piece 32 may be configured to be capable of rotating relatively to each other, and may also be configured to be not capable of rotating. The bent pipe 36 and the second tube piece 32 may also be formed integrally. An anti-suffocation valve plate 361 may be disposed inside the bent pipe 36, to ensure the unidirectional flowing of the gas. In such a case, the tube assembly 30 is connected to the frame 211 by the bent pipe 36.

In the present disclosure, the opening and closing of the outlet end of the first tube piece 31 and the opening and closing of the discharging hole 311 may also be automatically controlled. For example, after the first tube piece 31 and the second tube piece 32 have been connected, an electric signal may be generated (for example, by using a loop connection, a sensor, a touch switch and so on), and the signal controls the outlet end of the first tube piece 31 to open and the discharging hole 311 to close. After the first tube piece 31 and the second tube piece 32 have been separated, the connection between the first tube piece 31 and the second tube piece 32 is broken, and no electric signal is generated, at which point the outlet end of the first tube piece 31 is closed, and the discharging hole 311 is opened, to discharge the gas at a controllable flow rate.

In the present disclosure, the parameters of the discharging hole 311 (such as the quantity, the diameter thickness, the hole inner cone, the outer cone and the hydrophobic material) may be particularly set to further control the flow rate and reduce the noise. For example, when the discharging hole 311 is disposed in the tube wall of the first tube piece 31, one of the inner wall surface and the outer wall surface of the tube wall may be formed by using a hydrophobic material or a hydrophilic material, or be spread-coated with a hydrophobic material or a hydrophilic material. The other of the wall surfaces may be formed or spread-coated by the other of a hydrophobic material and a hydrophilic material. The discharging hole 311 may be configured to be of a structure in which the ventilation areas at the two ends are different, for example a trapezoid or a hourglass shape. Particularly, when the tube assembly 30 is applied to a breathing mask, the discharging hole 311 may be configured according to the depth of the mask in the direction of the sagittal section (cutting a human body into a left part and a right part, the section interface between the left part and the right part refers to a sagittal plane). When the depth is lower, or, in other words, the face of the patient has a lower distance from the discharging hole 311, it may be set that the proximal discharging-hole area is greater than the distal discharging-hole area, to prevent gas-flow intersection to make a large noise. When the depth is higher, or, in other words, the face of the patient has a higher distance from the discharging hole 311, it may be set that the proximal discharging-hole area is greater than the distal discharging-hole area, which facilitates the dissipation of the discharged gas. In addition, a turbulent member (for example, a spoiler) may be disposed between the proximal component and the distal component, thereby reducing the noise of the gas discharging.

In the present disclosure, the quantity, the size, the spacing and the overall layout of the discharging holes 311 may have various embodiments. For example, the diameter of the discharging hole 311 may range 0.4 mm-1.5 mm, preferably 0.6 mm-0.8 mm. The thickness of the position where the discharging hole 311 is disposed may be 1 mm-20 mm.

Another aspect of the present disclosure provides a ventilation-treatment method, wherein the method is performed by using the ventilation-treatment apparatus stated above, and the method includes the following steps:

generating a first signal when the first valve assembly and the second valve assembly contact, and according to the first signal, controlling the mainframe 40 to start up or increase the ventilation capacity (i.e., increasing the gas flow rate from the mainframe 40 to the ventilation pipeline 50); and/or generating a second signal when the first valve assembly and the second valve assembly are separated, and according to the second signal, controlling the mainframe 40 to shut down or reduce the ventilation capacity (i.e., reducing the gas flow rate from the mainframe 40 to the ventilation pipeline 50).

In the present disclosure, the action of the mainframe 40 preferably happens after the actions of the first valve body 13 and the second valve body 23. In addition, the method may further include: after the mainframe 40 has been started up, when the head band 22 and the headrest 10 disengage, enabling the ventilation-treatment apparatus to emit an alarm; according to the first signal, controlling the first valve body 13 and the second valve body 23 to move to the opening position; and according to the second signal, controlling the first valve body 13 and the second valve body 23 to move to the closing position.

In the present disclosure, in order to generate the first signal and the second signal, a heat sensing device or a pressure detecting device may be disposed at the headrest 10. In usage, when the heat sensing device has sensed heat within a particular distance range, or when the pressure detecting device has detected the pressure by the head of the patient, the first signal is generated. When the heat sensing device does not sense heat within the particular distance range, or when the pressure detecting device does not detect the pressure by the head of the patient, the second signal is generated. It may be understood that the heat sensing device or the pressure detecting device may also be disposed at any other suitable position, for example a mattress.

According to an embodiment of the present disclosure, the pressure detecting device is disposed at the surface of the headrest 10. When the patient lies down and prepares to accept the treatment, the head band 22 and the headrest 10 contact, and the first valve body 13 and the second valve body 23 automatically move to the opening position under the pressure of the head, to form a ventilation channel. At this point, the pressure detecting device detects the pressure, generates the first signal, and controls the mainframe 40 to start to operate in turn according to the first signal. When the patient gets up, the head band 22 and the headrest 10 are separated, and the first valve body 13 and the second valve body 23 automatically move to the closing position. At this point, the pressure detecting device does not detect the pressure, generates the second signal, and controls the mainframe 40 to stop operating in turn according to the second signal.

The automatic ventilation-treatment method using the ventilation-treatment apparatus has been described above. It should be noted that, in usage, the patient may select manual treatment or automatic treatment according to demands, wherein the manual treatment refers to that the actions of the mainframe 40 (such as starting-up and shutting-down) are manually controlled.

The preferable embodiments of the present disclosure have been described in detail above with reference to the drawings. However, the present disclosure is not limited to the particular details of the above embodiments. Within the scope of the technical concept of the present disclosure, the technical solutions of the present disclosure may have various simple variations, and all of those simple variations fall within the protection scope of the present disclosure.

In addition, it should be noted that the particular technical features described in the particular embodiments, subject to no contradiction, may be combined in any feasible way. In order to avoid unnecessary repeating, the feasible modes of combination will not be described further herein.

Furthermore, the different embodiments of the present disclosure may also be combined in any way, and, as long as the combinations do not depart from the concept of the present disclosure, they should also be considered as the contents disclosed by the present disclosure.

The above-described device embodiments are merely illustrative, wherein the units that are described as separate components may or may not be physically separate, and the components that are displayed as units may or may not be physical units; in other words, they may be located at the same one location, and may also be distributed to a plurality of network units. Some or all of the modules may be selected according to the actual demands to implement the purposes of the solutions of the embodiments. A person skilled in the art can understand and implement the technical solutions without paying creative work.

The "one embodiment", "an embodiment" or "one or more embodiments" as used herein means that particular features, structures or characteristics described with reference to an embodiment are included in at least one embodiment of the present disclosure. Moreover, it should be noted that here an example using the wording "in an embodiment" does not necessarily refer to the same one embodiment.

The description provided herein describes many concrete details. However, it can be understood that the embodiments of the present disclosure may be implemented without those concrete details. In some of the embodiments, well-known processes, structures and techniques are not described in detail, so as not to affect the understanding of the description.

In the claims, any reference signs between parentheses should not be construed as limiting the claims. The word "comprise" does not exclude elements or steps that are not listed in the claims. The word "a" or "an" preceding an element does not exclude the existing of a plurality of such elements. The present disclosure may be implemented by means of hardware comprising several different elements and by means of a properly programmed computer. In unit claims that list several devices, some of those devices may be embodied by the same item of hardware. The words first, second, third and so on do not denote any order. Those words may be interpreted as names.

Finally, it should be noted that the above embodiments are merely intended to explain the technical solutions of the present disclosure, and not to limit them. Although the present disclosure is explained in detail with reference to the above embodiments, a person skilled in the art should understand that he can still modify the technical solutions set forth by the above embodiments, or make equivalent substitutions to part of the technical features of them. However, those modifications or substitutions do not make the essence of the corresponding technical solutions depart from the spirit and scope of the technical solutions of the embodiments of the present disclosure.

The invention claimed is:

1. A tube assembly for connecting to a ventilation-treatment apparatus with a gas source, wherein the tube assembly comprises a first tube piece and a second tube piece, the tube assembly is provided with a connecting state in which the first tube piece and the second tube piece are coaxially plug-connected and a separating state in which the first tube piece and the second tube piece are separated from each other;

wherein the first tube piece is provided with an inlet end for connecting the gas source and an outlet end for connecting the second tube piece; the first tube piece comprises a discharging hole, and the discharging hole is configured so that, in the connecting state, the discharging hole is closed to make the gas from the gas source to enter the second tube piece, and in the separating state, the discharging hole is opened to make the gas from the gas source to be discharged outside from the discharging hole; and the tube assembly further comprises a valve member, and the valve member is configured so that, in the connecting state, the valve member opens the outlet end of the first tube piece to make the gas from the gas source to enter the second tube piece, and in the separating state, the valve member closes the outlet end to make the gas from the gas source to be discharged outside from the discharging hole.

2. The tube assembly according to claim 1, wherein the valve member comprises a valve core that is movably disposed inside the first tube piece in an axial direction of the first tube piece, the discharging hole is disposed in a tube wall of the first tube piece, and the second tube piece is disposed with a gas flowing channel;

wherein the tube assembly is configured so that, in the connecting state, the valve core moves to an upstream position of the discharging hole in a flowing direction of the gas, a part of the second tube piece that protrudes into the first tube piece forms, together with the valve core, the valve member to close the discharging hole, and the first tube piece communicates with the second tube piece via the gas flowing channel; and in the separating state, the valve core moves to a downstream position of the discharging hole in the flowing direction of the gas to close the outlet end of the first tube piece.

3. The tube assembly according to claim 2, wherein the valve core is a cylindrical body or a spherical body, and the first tube piece is configured to be of a non-constant-diameter structure.

4. The tube assembly according to claim 2, wherein the valve member further comprises a valve-core stopper disposed inside the first tube piece, and the valve-core stopper is configured to limit the valve core.

5. The tube assembly according to claim 4, wherein the valve-core stopper is an annular boss disposed on an inner wall of the first tube piece, when the tube assembly is in the connecting state, a right side surface of the valve core abuts a left side surface of the annular boss, or a gap exists between the right side surface of the valve core and the left side surface of the annular boss, wherein the gap is less than the axial length of the valve core.

6. The tube assembly according to claim 5, wherein the gap between the right side surface of the valve core and the left side surface of the annular boss is less than the maximum diameter of the valve core.

7. The tube assembly according to claim 2, wherein a center of gravity of the valve core is deviated to right.

8. The tube assembly according to claim 1, wherein in the connecting state, the first tube piece and the second tube piece are configured to rotate relative to each other, and the tube assembly further comprises a connecting structure for connecting the first tube piece and the second tube piece.

9. The tube assembly according to claim 8, wherein the connecting structure comprises a clip and a clipping slot matched with each other, the clip is disposed at one of the first tube piece and the second tube piece and the clipping slot is disposed at the other one of the first tube piece and the second tube piece.

10. The tube assembly according to claim 9, wherein the clipping slot is disposed on an outer wall surface of the second tube piece, the clip is configured to be rotatably connected to an outer wall surface of the first tube piece, and the clip is configured to swing in a radial direction of the first tube piece to be snap-fitted to or separated from the clipping slot; and wherein the tube assembly further comprises a limiting member that is configured for preventing the clip from disengaging from the clipping slot when the clip is snap-fitted to the clipping slot.

11. The tube assembly according to claim 10, wherein the limiting member is a lantern ring that is movably nested outside the first tube piece or the second tube piece in the axial direction of the first tube piece.

12. The tube assembly according to claim 10, wherein the clipping slot is an L-shaped slot disposed in the tube wall of the second tube piece, the L-shaped slot comprises an axial part and a radial part, the clip is a cylindrical piece that is protrusively disposed on the tube wall of the first tube piece, and the cylindrical piece is configured to, when the first tube piece and the second tube piece are plug-connected, enter the axial part and move to the radial part to implement the snap fitting; and wherein the limiting member is a lug disposed inside the radial part, and the lug is configured to releasably stop the cylindrical piece.

13. The tube assembly according to claim 9, wherein the connecting structure further comprises a plurality of clips and a plurality of clipping slots, the plurality of clips and the plurality of clipping slots are disposed separately in circumferential directions of the first tube piece and the second tube piece, respectively.

14. The tube assembly according to claim 8, wherein the connecting structure comprises a first protrusion and a second protrusion matched with each other, the first protrusion is disposed on the inner wall surface or the outer wall surface of the first tube piece, the second protrusion is disposed on the outer wall surface or the inner wall surface of the second tube piece; and wherein the first protrusion is configured to be T-shaped, the second protrusion comprises two convex parts that are separated in the circumferential direction of the second tube piece, when the second tube piece is plug-connected to the first tube piece, the first protrusion and the second protrusion face each other axially to implement a snap fitting, so that an axial part of the first protrusion is snap-fitted between the two convex parts.

15. The tube assembly according to claim 8, wherein the connecting structure is configured as one of the following:

the connecting structure comprises a first magnet and a second magnet with opposite magnetic poles, the first magnet is provided at one of the first tube piece and the second tube piece, and the second magnet is provided at the other one of the first tube piece and the second tube piece, and a connection is implemented by the attraction between the first magnet and the second magnet in response to the first tube piece and the second tube piece being plug-connected; or the connecting structure comprises a first thread and a second thread matched with each other, the first thread is disposed at one of the first tube piece and the second tube piece, and the second thread is disposed at the other one of the first tube piece and the second tube piece.

16. The tube assembly according to claim 1, wherein the tube assembly further comprises a bent pipe connected to an end of the second tube piece, and the bent pipe and the second tube piece are configured to be rotatable relatively to each other, and an anti-suffocation valve plate is disposed inside the bent pipe to ensure an unidirectional flowing of the gas.

17. The tube assembly according to claim 1, wherein the valve member comprises a valve plate rotatably disposed inside the first tube piece, a rotation axis of the valve plate is perpendicular to an axial direction of the first tube piece; and wherein the valve plate is configured to rotate between a first position where the discharging hole is closed and the outlet end of the first tube piece is opened and a second position where the discharging hole is opened and the outlet end of the first tube piece is closed.

18. The tube assembly according to claim 17, wherein the valve plate is further configured so that, in the second position, an edge of the valve plate abuts an inner wall surface of the first tube piece, and the discharging hole is disposed in one of the valve plate and a tube wall of the first tube piece, or the valve plate is further configured so that, in the second position, a gap exists between an edge of the valve plate and the inner wall surface of the first tube piece, and the gap forms the discharging hole.

19. The tube assembly according to claim 17, wherein the valve plate is connected to a top of a tube wall of the first tube piece, and the discharging hole is disposed at a bottom of the tube wall of the first tube piece.

20. The tube assembly according to claim 19, wherein in response to the second tube piece being inserted into the first tube piece, the second tube piece pushes the valve plate to the first position to open the outlet end of the first tube piece, and the tube wall of the second tube piece blocks the discharging hole.

* * * * *